(12) United States Patent
Chen et al.

(10) Patent No.: US 10,322,178 B2
(45) Date of Patent: Jun. 18, 2019

(54) SYSTEMS AND METHODS FOR TARGETED DRUG DELIVERY

(71) Applicants: The Trustees of Columbia University in the City of New York, New York, NY (US); The University of North Carolina at Chapel Hill, Chapel Hill, NC (US)

(72) Inventors: Chen Chen, New York, NY (US); Elisa E. Konofagou, New York, NY (US); Paul Dayton, Chapel Hill, NC (US)

(73) Assignees: The Trustees of Columbia University in the City of New York, New York, NY (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/457,023

(22) Filed: Aug. 11, 2014

(65) Prior Publication Data
US 2015/0045724 A1    Feb. 12, 2015

Related U.S. Application Data

(60) Provisional application No. 61/864,277, filed on Aug. 9, 2013, provisional application No. 61/864,285, filed on Aug. 9, 2013.

(51) Int. Cl.
*A61M 37/00*    (2006.01)
*A61K 41/00*    (2006.01)
(Continued)

(52) U.S. Cl.
CPC ........ *A61K 41/0047* (2013.01); *A61K 9/0009* (2013.01); *A61K 9/0019* (2013.01);
(Continued)

(58) Field of Classification Search
CPC ............ A61K 41/0047; A61K 9/0009; A61M 37/0092
(Continued)

(56) References Cited

U.S. PATENT DOCUMENTS

| 3,598,111 A | 8/1971 | Kahn |
| 4,463,608 A | 8/1984 | Takeuchi et al. |

(Continued)

FOREIGN PATENT DOCUMENTS

| EP | 0 221 409 | 5/1987 |
| EP | 0 627 206 | 12/1994 |

(Continued)

OTHER PUBLICATIONS

Sheeran et al. "Formulation and Acoustic Studies of a New Phase-Shift Agent for Diagnostic and Therapeutic Ultrasound". Jul. 11, 2011. Langmuir, 27 (17), pp. 10412-10420.*

(Continued)

*Primary Examiner* — Edelmira Bosques
*Assistant Examiner* — Leah J Swanson
(74) *Attorney, Agent, or Firm* — Baker Botts LLP

(57) ABSTRACT

Techniques for opening a target tissue using nanodroplets are provided. An exemplary method can include targeting a region of tissue for opening, delivering a plurality of nanodroplets to the region, and applying an ultrasound beam at the region such that the nanodroplets cavitate, or convert to microbubbles that cavitate, thereby causing the target tissue to open.

26 Claims, 21 Drawing Sheets

100

Targeting a region of tissue for opening
110

Delivering a plurality of nanobubbles to the region
120

Applying an ultrasound beam at the region
130

(51) Int. Cl.
*A61B 17/20* (2006.01)
*A61K 9/00* (2006.01)
*A61K 9/50* (2006.01)
*A61K 9/51* (2006.01)
*A61N 7/00* (2006.01)
*A61B 17/22* (2006.01)

(52) U.S. Cl.
CPC .......... *A61K 9/0043* (2013.01); *A61K 9/5031* (2013.01); *A61K 9/5146* (2013.01); *A61M 37/0092* (2013.01); *A61N 7/00* (2013.01); *A61B 2017/22008* (2013.01); *A61N 2007/0039* (2013.01)

(58) Field of Classification Search
USPC .......................................................... 604/22
See application file for complete search history.

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,882,679 A | 11/1989 | Tuy et al. |
| 4,926,675 A | 5/1990 | Schohl et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Iinuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,722,411 A | 3/1998 | Suzuki et al. |
| 5,741,522 A | 4/1998 | Violante et al. |
| 5,752,515 A | 5/1998 | Jolesz et al. |
| 5,769,790 A | 6/1998 | Watkins et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plews |
| 6,259,943 B1 | 7/2001 | Cosman et al. |
| 6,270,459 B1 | 8/2001 | Konofagou et al. |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,867 B1 | 7/2002 | Vaezy et al. |
| 6,447,450 B1 | 9/2002 | Oldstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,514,221 B2 | 2/2003 | Hynynen et al. |
| 6,529,770 B1 | 3/2003 | Grimblatov |
| 6,537,217 B1 | 3/2003 | Bjærum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu |
| 6,770,033 B1 | 8/2004 | Fink et al. |
| 6,875,176 B2 | 4/2005 | Mourad et al. |
| 6,936,151 B1 | 8/2005 | Lock et al. |
| 6,994,673 B2 | 2/2006 | Lysyansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson et al. |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,208,709 B2 | 6/2012 | Ding et al. |
| 8,257,338 B2 | 9/2012 | Keenan et al. |
| 9,063,220 B2 | 6/2015 | Yoda et al. |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0193784 A1 | 12/2002 | McHale et al. |
| 2003/0097068 A1 | 5/2003 | Hossack et al. |
| 2003/0125621 A1 | 7/2003 | Drukker et al. |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2004/0006266 A1 | 1/2004 | Ustuner et al. |
| 2004/0049134 A1 | 3/2004 | Tosaya et al. |
| 2004/0054357 A1 | 3/2004 | O'Donnell |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0172081 A1 | 9/2004 | Wang |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0249580 A1 | 12/2004 | Pourcelot et al. |
| 2004/0258760 A1 | 12/2004 | Wheatley et al. |
| 2005/0004466 A1 | 1/2005 | Hynenen et al. |
| 2005/0026262 A1* | 2/2005 | Yoshitani .................. C02F 1/34 435/167 |
| 2005/0054930 A1 | 3/2005 | Rickets et al. |
| 2005/0059876 A1 | 3/2005 | Krishnan |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1 | 6/2005 | Weitzel et al. |
| 2005/0175541 A1 | 8/2005 | Lanza et al. |
| 2005/0201942 A1 | 9/2005 | Dugstad et al. |
| 2005/0203395 A1 | 9/2005 | Sui et al. |
| 2005/0203399 A1 | 9/2005 | Vaezy et al. |
| 2005/0259864 A1 | 11/2005 | Dickinson et al. |
| 2005/0267695 A1 | 12/2005 | German |
| 2005/0277824 A1 | 12/2005 | Aubry et al. |
| 2005/0277835 A1 | 12/2005 | Angelsen et al. |
| 2006/0034904 A1 | 2/2006 | Weimann |
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241529 A1 | 10/2006 | Hynynen et al. |
| 2007/0049824 A1 | 3/2007 | Konofagou et al. |
| 2007/0055179 A1 | 3/2007 | Deem et al. |
| 2007/0059247 A1 | 3/2007 | Lindner et al. |
| 2007/0071683 A1* | 3/2007 | Dayton .............. A61K 41/0028 424/9.5 |
| 2007/0129652 A1 | 6/2007 | Nita |
| 2007/0207194 A1 | 9/2007 | Grayburn et al. |
| 2007/0219447 A1 | 9/2007 | Kanai et al. |

(56) References Cited

U.S. PATENT DOCUMENTS

| | | |
|---|---|---|
| 2007/0232962 A1 | 10/2007 | Zumeris et al. |
| 2007/0239001 A1 | 10/2007 | Mehi et al. |
| 2007/0276242 A1 | 11/2007 | Konofagou et al. |
| 2007/0276245 A1 | 11/2007 | Konofagou et al. |
| 2007/0276254 A1 | 11/2007 | Konofagou |
| 2008/0089848 A1 | 4/2008 | DiMauro |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0056924 A1 | 3/2010 | Powers |
| 2010/0286527 A1 | 11/2010 | Cannon et al. |
| 2011/0028854 A1 | 2/2011 | Addison et al. |
| 2011/0098562 A1 | 4/2011 | Salgo et al. |
| 2011/0177005 A1* | 7/2011 | Rapoport ............. A61K 9/0009 424/9.37 |
| 2011/0208038 A1 | 8/2011 | Konofagou et al. |
| 2011/0295105 A1* | 12/2011 | Konofagou ............. A61N 7/00 600/411 |
| 2011/0313328 A1* | 12/2011 | Nita ....................... A61N 7/022 601/2 |
| 2012/0004693 A1 | 1/2012 | Lo et al. |
| 2013/0038479 A1 | 2/2013 | Eldar et al. |
| 2013/0046229 A1 | 2/2013 | Konofagou et al. |
| 2013/0066211 A1 | 3/2013 | Konofagou et al. |
| 2013/0131495 A1 | 5/2013 | Konofagou et al. |
| 2013/0195313 A1 | 8/2013 | Gauthier et al. |
| 2013/0204166 A1 | 8/2013 | Villanueva et al. |
| 2013/0289398 A1 | 10/2013 | Borden et al. |
| 2013/0304407 A1 | 11/2013 | George et al. |
| 2013/0315491 A1 | 11/2013 | Konofagou et al. |
| 2014/0114216 A1 | 4/2014 | Konofagou et al. |

FOREIGN PATENT DOCUMENTS

| | | |
|---|---|---|
| WO | WO 1999/037938 | 7/1999 |
| WO | WO 2005/030171 | 4/2005 |
| WO | WO 2007/0148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/030819 A1 | 3/2010 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |

OTHER PUBLICATIONS

Hynynen et al., "Local and reversible blood-brain barrier disruption by noninvasive focused ultrasound at frequencies suitable for trans-skull sonications" *NeuroImage* 24 (2005) 12-20.
Kawabata, et al., "Chemo-thermal approach for efficient ultrasonic tumor treatment with phase change nano droplet", *IEEE Int. Ultrasonics Symp.*, Oct. 18-21, 2011 Orlando, Florida, pp. 9-12
U.S. Appl. No. 11/433,510, filed May 12, 2006, U.S. Pat. No. 8,858,441, Oct. 14, 2014.
U.S. Appl. No. 11/697,573, filed Apr. 6, 2007, US 2007/0276245, Nov. 29, 2007.
U.S. Appl. No. 11/697,579, filed Apr. 6, 2007, US 2007/0276242, Nov. 29, 2007.
U.S. Appl. No. 11/899,004, filed Aug. 30, 2007, U.S. Pat. No. 8,150,128, Apr. 3, 2012.
U.S. Appl. No. 12/077,612, filed Mar. 19, 2008, US 2009/0005711, Jan. 1, 2009.
U.S. Appl. No. 12/096,254, filed Nov. 26, 2008, US 2009/0221916, Sep. 3, 2009.
U.S. Appl. No. 13/019,029, filed Feb. 1, 2011, U.S. Pat. No. 8,428,687, Apr. 23, 2013.
U.S. Appl. No. 13/045,070, filed Mar. 10, 2011, US 2011/0295105, Dec. 1, 2011.
U.S. Appl. No. 13/353,148, filed Jan. 18, 2012, US 2013/0066211, Mar. 14, 2013.
U.S. Appl. No. 13/426,400, filed Mar. 21, 2012, US 2013/0046229, Feb. 21, 2013.
U.S. Appl. No. 13/529,239, filed Jun. 21, 2012, US 2013/0131495, May 23, 2013.
U.S. Appl. No. 13/848,436, filed Mar. 21, 2013, US 2013/0315491, Nov. 28, 2013.
U.S. Appl. No. 14/091,010, filed Nov. 26, 2013, US 2014/0114216, Apr. 24, 2014.
U.S. Appl. No. 14/300,106, filed Jun. 9, 2014, US 2015/0010222, Jan. 8, 2015.
U.S. Appl. No. 14/476,543, filed Sep. 3, 2014, US 2015/0065871, Mar. 5, 2015.
U.S. Appl. No. 11/433,510, Jul. 23, 2014 Issue Fee Payment.
U.S. Appl. No. 11/433,510, Apr. 23, 2014 Notice of Allowance.
U.S. Appl. No. 11/433,510, Apr. 7, 2014 Applicant Initiated Interview Summary.
U.S. Appl. No. 11/433,510, Apr. 4, 2014 Response to Non-Final Office Action.
U.S. Appl. No. 11/433,510, Oct. 4, 2013 Non-Final Office Action.
U.S. Appl. No. 11/433,510, Mar. 30, 2012 Request for Continued Examination (RCE).
U.S. Appl. No. 11/433,510, Mar. 28, 2012 Advisory Action.
U.S. Appl. No. 11/433,510, Dec. 29, 2011 Response to Final Office Action.
U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510, Mar. 17, 2009 Non-Final Office Action.
U.S. Appl. No. 11/697,573, Jan. 12, 2015 Notice of Abandonment.
U.S. Appl. No. 11/697,573, Jun. 16, 2014 Non-Final Office Action.
U.S. Appl. No. 11/697,573, Oct. 17, 2013 Final Office Action.
U.S. Appl. No. 11/697,573, Sep. 4, 2013 Response to Non-Final Office Action.
U.S. Appl. No. 11/697,573, May 10, 2013 Non-Final Office Action.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/697,573, Aug. 18, 2011 Amendment and Request for Continued Examination (RCE).
U.S. Appl. No. 11/697,573, Mar. 18, 2011 Final Office Action.
U.S. Appl. No. 11/697,573, Dec. 22, 2010, Response to Non-Final Office Action.
U.S. Appl. No. 11/697,573, Jun. 23, 2010 Non-Final Office Action.
U.S. Appl. No. 11/697,579, Nov. 28, 2011 Notice of Abandonment.
U.S. Appl. No. 11/697,579, Apr. 29, 2011 Final Office Action.
U.S. Appl. No. 11/697,579, Feb. 7, 2011 Response to Non-Final Office Action.

(56) References Cited

OTHER PUBLICATIONS

U.S. Appl. No. 11/697,579, Aug. 6, 2010 Non-Final Office Action.
U.S. Appl. No. 11/697,579, May 17, 2010 Response to Non-Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579 Jul. 18, 2008 Non-Final Office Action.
U.S. Appl. No. 11/899,004, Jan. 3, 2012 Issue Fee payment.
U.S. Appl. No. 11/899,004, Oct. 4, 2012 Amendment after Allowance.
U.S. Appl. No. 11/899,004, Oct. 3, 2012 Notice of Allowance.
U.S. Appl. No. 11/899,004, Nov. 3, 2011 Decision on Petition.
U.S. Appl. No. 11/899,004, Oct. 4, 2011 Petition and Amendment after Notice of Allowance.
U.S. Appl. No. 11/899,004, Oct. 3, 2011 Notice of Allowance.
U.S. Appl. No. 11/899,004, Sep. 23, 2011 Amendment and Request for Continued Examination (RCE).
U.S. Appl. No. 11/899,004, Sep. 19, 2011 Decision on Petition.
U.S. Appl. No. 11/899,004, Jul. 18, 2011 Notice of Allowance.
U.S. Appl. No. 11/899,004, May 10, 2011 Response to Non-Final Office Action.
U.S. Appl. No. 11/899,004, Feb. 8, 2011 Non-Final Office Action.
U.S. Appl. No. 12/077,612, Oct. 29, 2015 Notice of Abandonment.
U.S. Appl. No. 12/077,612, Apr. 9, 2015 Non-Final Office Action.
U.S. Appl. No. 12/077,612, Sep. 22, 2014 Amendment and Request for Continued Examination (RCE).
U.S. Appl. No. 12/077,612, Jan. 30, 2014 Response to Non-Final Office Action.
U.S. Appl. No. 12/077,612, Jan. 2, 2014 Applicant Initiated Interview Summary.
U.S. Appl. No. 12/077,612, Aug. 30, 2013 Non-Final Office Action.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/07,7612, Nov. 16, 2010 Non-Final Office Action.
U.S. Appl. No. 12/077,612, Mar. 21, 2014 Final Office Action.
U.S. Appl. No. 12/096,254, Sep. 28, 2015 Notice of Abandonment.
U.S. Appl. No. 12/096,254, Feb. 27, 2015 Non-Final Office Action.
U.S. Appl. No. 12/096,254, Sep. 22, 2014 Amendment and Request for Continued Examination (RCE).
U.S. Appl. No. 12/096,254, Dec. 23, 2013 Response to Non-Final Office Action.
U.S. Appl. No. 12/096,254, Dec. 17, 2013 Applicant Initiated Interview Summary.
U.S. Appl. No. 12/096,254, Aug. 23, 2013 Non-Final Office Action.
U.S. Appl. No. 12/096,254, Nov. 30, 2012 Amendment and Request for Continued Examination (RCE).
U.S. Appl. No. 12/096,254, May 31, 2012 Final Office Action.
U.S. Appl. No. 12/096,254, Apr. 4, 2012 Response to Non-Final Office Action.
U.S. Appl. No. 12/096,254, Oct. 5, 2011 Non-Final Office Action.
U.S. Appl. No. 12/096,254, Mar. 21, 2014 Final Office Action.
U.S. Appl. No. 13/019,029, Mar. 21, 2013 Issue Fee payment.
U.S. Appl. No. 13/019,029, Dec. 26, 2012 Notice of Allowance.
U.S. Appl. No. 13/045,070, Nov. 17, 2015 Response after Final Action.
U.S. Appl. No. 13/045,070, Jul. 7, 2015 Final Office Action.
U.S. Appl. No. 13/045,070, May 18, 2015 Applicant Initiated Interview Summary.
U.S. Appl. No. 13/045,070, May 15, 2015 Response to Non-Final Office Action.
U.S. Appl. No. 13/045,070, Jan. 16, 2015 Non-Final Office Action.
U.S. Appl. No. 13/045,070, Nov. 7, 2013 Amendment and Request for Continued Examination (RCE).
U.S. Appl. No. 13/045,070, May 9, 2013 Final Office Action.
U.S. Appl. No. 13/045,070, Dec. 21, 2012 Response to Non-Final Office Action.
U.S. Appl. No. 13/045,070, Jun. 22, 2012 Non-Final Office Action.
U.S. Appl. No. 13/353,148, Aug. 12, 2015 Non-Final Office Action.
U.S. Appl. No. 13/353,148, Jul. 6, 2015 Amendment and Request for Continued Examination (RCE).
U.S. Appl. No. 13/353,148, Mar. 3, 2015 Final Office Action.
U.S. Appl. No. 13/353,148, Oct. 24, 2014 Response to Non-Final Office Action.
U.S. Appl. No. 13/353,148 Oct. 14, 2014, Applicant Initiated Interview Summary.
U.S. Appl. No. 13/353,148, Apr. 24, 2014 Non-Final Office Action.
U.S. Appl. No. 13/353,148, Apr. 17, 2014 Amendment and Request for Continued Examination (RCE).
U.S. Appl. No. 13/353,148, Feb. 25, 2014 Applicant Initiated Interview Summary.
U.S. Appl. No. 13/353,148, Oct. 17, 2013 Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 13/426,400, Dec. 4, 2015 Applicant Initiated Interview Summary.
U.S. Appl. No. 13/426,400, Dec. 4, 2015 Response to Non-Final Office Action.
U.S. Appl. No. 13/426,400, Jul. 2, 2015 Non-Final Office Action.
U.S. Appl. No. 13/426,400, Mar. 23, 2015 Amendment and Request for Continued Examination (RCE).
U.S. Appl. No. 13/426,400, Dec. 23, 2014 Final Office Action.
U.S. Appl. No. 13/426,400, Oct. 2, 2014 Response to Non-Final Office Action.
U.S. Appl. No. 13/426,400, May 5, 2014 Non-Final Office Action.
U.S. Appl. No. 13/529,239, Jun. 4, 2015 Final Office Action.
U.S. Appl. No. 13/529,239, Mar. 5, 2015 Applicant Initiated Interview Summary.
U.S. Appl. No. 13/529,239, Mar. 3, 2015 Response to Non-Final Office Action.
U.S. Appl. No. 13/529,239, Sep. 3, 2014 Non-Final Office Action.
U.S. Appl. No. 13/529,239, Jun. 30, 2014 Amendment and Request for Continued Examination (RCE).
U.S. Appl. No. 13/529,239, May 1, 2014 Applicant Initiated Interview Summary.
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Nov. 18, 2013 Applicant Initiated Interview Summary.
U.S. Appl. No. 13/529,239, Jul. 5, 2013 Non-Final Office Action.
"Vial", Retrieved from http://en.wikipedia.org/w/index.php?title=Vial&oldid=603936258.[Downloaded on May 20, 2014].
Abbott, et al., "Astrocyte-Endothelial Interactions at the Blood-Brain Barrier", *Nat. Rev. Neurosci.*, 7(1):41-53 (2006).
Ammi, et al., "Ultrasonic contrast agent shell rupture detected by inertial cavitation and.rebound signals", *IEEE Transactions*, 53(1):126-136 (2006).
Ashikaga, et al., "Transmural Dispersion of Myofiber Mechanics: Implications for Electrical Heterogeneity In Vivo", *Journal of the American College of Cardiology*, 49(8):909-916 (2007).
Aubry, et al., "Experimental Demonstration of Noninvasive Transskull Adaptive.Focusing Based on Prior Computed Tomography Scans", *The Journal of the Acoustical Society of America*, 113:84 (2003).
Avolio, et al., "Effects of aging on changing arterial compliance and left ventricular load in a northern Chinese urban community", *Circulation*, 68(1):50-58 (1983).
Azuma, et al., "Bubble Generation by Standing Wave in Water Surrounded by Cranium.With Transcranial Ultrasonic Beam", *Japanese Journal of Applied Physics*, 44:4625-4630.
Badke, et al., "Effects of Ventricular Pacing on Regional Left Ventricular Performance In the Dog", *Am J Physiol Heart Circ Physiol.*, 238:H858-867 (1980).

(56) References Cited

OTHER PUBLICATIONS

Baron, et al., "Simulation of Intracranial Acoustic Fields in Clinical Trials of Sonothrombolysis", *Ultrasound Med. Biol.*, 35(7):1148-1158 (2009).

Baseri, et al., "Multi-Modality Safety Assessment of Blood-Brain Barrier Opening Using Focused Ultrasound and Definity Microbubbles: A Short-Term Study", *Ultrasound Med. Biol.*, 6(9):1445-1459 (2010).

Behrens, et al., "Low-Frequency, Low-Intensity Ultrasound Accelerates Thrombolysis Through the Skull", *Ultrasound in Medicine & Biology*, 25:269-273 (1999).

Bercoff, et al., "Supersonic Shear Imaging: A New Technique for Soft Tissue Elasticity Mapping", *IEEE Transactions on Ultrasonics Ferroelectrics and Frequency Control*, 51:396-409 (2004).

Berger, et al., "Single-Beat Noninvasive Imaging of Cardiac Electrophysiology of Ventricular Pre-Excitation", *Journal of the American College of Cardiology*, 48:2045-2052 (2006).

Bers, "Cardiac Excitation-Contraction Coupling", *Nature*, 415:198-205 (2002).

Bonnefous, et al, "Time Domain Formulation of Pulse-Doppler Ultrasound and Blood Velocity Estimation by Cross Correlation", *Ultrason Imaging*, 8(2):73-85 (1986).

Borden et al., "Ultrasound Radiation Force Modulates Ligand Availability on Target Contrast Agents", Mol. Imaging, 5:139-147 (2006).

Brekke, et al., "Tissue Doppler Gated (TDOG) Dynamic Three-Dimensional Ultrasound Imaging of the Fetal Heart", *Ultrasound Obstet Gynecol.*, 24(2):192-198 (2004).

Brooks, et al., "Electrical Imaging of the Heart", *IEEE Signal Processing Magazine*, 14:24-42 (1997).

Brundin, et al., "Restorative Therapies in Parkinson's Disease", *Springer Verlag* (2006).

Campbell, et al., "Mechanisms of Transmurally Varying Myocyte Electromechanics in an Integrated Computational Model", *Philos Transact A Math Phys Eng Sci* ., 366:3361-3380 (2008).

Carman, et al., "Adenosine receptor signaling modulates permeability of the blood-brain barrier", The Journal of Neuroscience, 31(37):13272-13280 (2011).

Caskey, et al., "Direct Observations of Ultrasound Microbubble Contrast Agent Interaction With the Microvessel Wall", *J. Acoust. Soc. Amer.*, 122(2):1191-1200 (2007).

Caskey, et al., "Microbubble Oscillation in Tubes With Diameters of 12, 25, and 195 Microns", *Appl. Phys. Lett.*, 88(3):033902-1-033902-3 (2006).

Cavaglia, et al., "Regional Variation in Brain Capillary Density and Vascular Response to Ischemia", *Brain Res.*, 910(1-2):81-93 (2001).

Chan, "Transgenic Nonhuman Primates for Neurodegenerative Diseases", *Reproductive Biology and Endocrinology*, 2:39 (2004).

Chang, et al., "3-D US Frame Positioning Using Speckle Decorrelation and Image Registration", *Ultrasound in Medicine and Biology*, pp. 801-812 (2003).

Chen, et al., "The size of blood-brain barrier opening induced by focused ultrasound is dictated by the acoustic pressure", J. Cereb. Blood Flow Metab., 34:1197-1204 (2014).

Chen, et al., "Architectural Acoustics and Noise: Advancements and Best Practices in Instrumentation for Architectural Acoustics and Noise", *J. Acoust. Soc. Am.; 164th Meeting: Acoustical Society of America*, 132(3, Pt. 2):1977-2018 (Sep. 2012).

Chen, et al., "Engineering Acoustics and Asa Committee on Standards: Sound Intensity Measurements", *J. Acoust. Soc. Am.; 164th Meeting: Acoustical Society of America*, 132(3, Pt. 2):1984 (Sep. 2012).

Chen, et al., "Estimation of Displacement Vectors and Strain Tensors in Elastography Using Angular Insonifications", *IEEE Transactions on Medical Imaging*, 23(12):1479-1489 (2004).

Chen, et al., "Optimization of Ultrasound Parameters for Cardiac Gene Delivery of Adenoviral or Plasmid Deoxyribonucleic Acid by Ultrasound-Targeted Microbubble Destruction", *J. Amer. Coll. Cardiol.*, 42(2):301-308 (2003).

Choi, et al., "Feasibility of Transcranial, Localized Drug-Delivery in the Brain of Alzheimer's-Model Mice Using Focused Ultrasound", *2005 IEEE Ultrasonics Symposium*, pp. 988-991 (Sep. 18-21, 2005).

Choi, et al., "Microbubble-size dependence of focused ultrasound-induced blood-brain barrier opening in mice in vivo", *IEEE transactions on Biomedical Engineering*, 57(1):145-154 (2010).

Choi, et al., "Molecules of Various Pharmacologically—Relevant Sizes Can Cross the Ultrasound-Induced Blood-Brain Barrier Opening In Vivo", *Ultrasound in Medicine & Biology*, 36(1):58-67 (2009).

Choi, et al., "Noninvasive, Transcranial and Localized Opening of the Blood-Brain Barrier Using Focused Ultrasound in Mice", *Ultrasound in Medicine & Biology*, 33(1):95-104 (2007).

Choi, et al., "Spatio-Temporal Analysis of Molecular Delivery Through the Blood-Brain Barrier Using Focused Ultrasound", *Physics in Medicine and Biology*, 52:5509-5530, (2007).

Choi, et al., "Delivery of pharmacologically-relevant sized molecules through the ultrasound-induced blood-brain barrier opening in vivo", *Neuroscience, Chicago, IL, USA*, Oct. 17-21, 2009.

Choi, et al., "Focused Ultrasound-Induced Molecular Delivery Through the Blood-Brain Barrier", *Presented at the IEEE Symp. Ultrason. Ferroelect. Freq. Control, New York, NY*, pp. 1192-1195 (2007).

Choi, et al., "Noninvasive and Transient Blood-Brain Barrier Opening in the Hippocampus of Alzheimer's Double Transgenic Mice Using Pulsed Focused Ultrasound", *Ultrasonic Imaging*, pp. 189-200 (2008).

Choi, et al., "Optimization of Blood-Brain Barrier Opening in Mice using Focused Ultrasound", *2006 IEEE Ultrasounics Symposium* [online], Jun. 2007.

Chomas, et al., "Threshold of Fragmentation for Ultrasonic Contrast Agents", *J. Biomed. Opt.*, 6(2):141-150 (2001).

Clement, et al., "A Hemisphere Array for Non-Invasive Ultrasound Brain Therapy and Surgery", *Phys Med Biol.*, 45:3707-3719 (2000).

Cobbold, R.S.C., "Foundations of biomedical ultrasound", Biomedical engineering series, Oxford University Press, pp. 422-423(2006).

Connor, "Simulation Methods and Tissue Property Models for Non-Invasive Transcranial Focused Ultrasound Surgery", *Ph.D. Thesis* (2005).

Connor, et al., "A Unified Model for the Speed of Sound in Cranial Bone Based on Genetic Algorithm Optimization", *Physics in Medicine and Biology*, 47:3925-3944 (2002).

Cordeiro, et al., "Transmural Heterogeneity of Calcium Activity and Mechanical Function in the Canine Left Ventricle", *Am J Physiol. Heart Circ. Physiol.*, 286:H1471-1479 (2004).

Coyle, "Arterial Patterns of the Rat Rhinencephalon and Related Structures", *Exp. Neurol.*, 49(3): 671-690 (1975).

Coyle, "Spatial Features of the Rat Hippocampal Vascular System", *Exp. Neurol.*, 58(3): 549-561 (1978).

Coyle, "Vascular Patterns of the Rat Hippocampal Formation", *Exp. Neurol.*, 52(3): 447-458 (1976).

Crum, et al., "Bjerknes Forces on Bubbles in a Stationary Sound Field", *The Journal of the Acoustical Society of America*, 57(6): 1363-1370 (1975).

Cutnell, et al., (1998). Physics, Fourth Edition. New York. Table of Contents.

Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", *Stroke*, 36:1441-146 (2005).

Damianou, et al., "Dependence of ultrasonic attenuation and absorption in dog soft tissues on temperature and thermal dose", *J Acoust Soc Am*, 102(1):628-634 (1997).

Datta, et al., "Correlation of Cavitation With Ultrasound Enhancement of Thrombolysis", *Ultrasound in Medicine & Biology*, 32(8): 1257-1267 (2006).

De Craene, et al., "Temporal diffeomorphic free-form deformation: Application to motion and strain estimation from 3D echocardiography", Medical Image Analysis, 16(2):427-450 (2012).

(56) References Cited

OTHER PUBLICATIONS

Declerck, et al., "Left ventricular motion reconstruction from planar tagged MR images: a comparison", *Phys Med Biol* ., 45(6): 1611-1632 (2000).
Deffieux, et al., "Transcranial Focused Ultrasound for Blood-Brain Barrier Opening—Numerical Simulations With In Vitro Validation in Human and Monkey Skulls", Title page And Table of Contents for the AIUM Annual Convention, San Diego, CA, (2010).
Definition of "spatial filter" retrieved from http://ww.onelook.com/ on May 26, 2015.
DeLong, "Primate Models of Movement Disorders of Basal Ganglia Origin", *Trends Neurosci.*, 13(7): 281-285 (1990).
DuBose, et al., "Confusion and Direction in Diagnostic Doppler Sonography", Journal of Diagnostic Medical Sonography, 25(3):173-177 (2009).
Duck, "Physical Properties of Tissue: A Comprehensive Reference Book", *Academic Press, London, UK*, 1990.
Duerinckx, et al., "In vivo acoustic attenuation in liver: correlations with blood tests and histology", *Ultrasound Imaging*, 14(5):405-413 (1988).
Durrer, et al., "Total Excitation of the Isolated Human Heart", *Circulation*, 41:899-912 (1970).
Edwards, et al., "Effects of Ischemia on Left-Ventricular Regional Function in the Conscious Dog", *American Journal of Physiology*, 240, H413-H420 (1981).
EPO Search Report and Opinion and Office Action for EP0684017.2 dated Dec. 7, 2009 and Mar. 8, 2010.
Epstein-Barasg, et al., A microcomposite hydrogel for repeated on-demand ultrasound-triggered drug delivery, Biomaterials, 31(19):5208-5217 (2010)
Erpelding, et al., "Bubble-Based Acoustic Radiation Force Using Chirp Insonation to Reduce Standing Wave Effects", *Ultrasound in Medicine & Biology*, 33(2):263-269 (2007).
European Search Report for EP Application No. 10838238, dated May 6, 2014.
Everbach, et al., "Cavitational Mechanisms in Ultrasound-Accelerated Thrombolysis at 1 Mhz", *Ultrasound in Medicine & Biology*, 26(7): 1153-1160 (2000).
Faris, et al., "Novel Technique for Cardiac Electromechanical Mapping With Magnetic Resonance Imaging Tagging and an Epicardial Electrode Sock", *Ann Biomed Eng.*, 31:430-440 (2003).
Farook, et al., "Preparation of Microbubble Suspensions by Co-Axial Electrohydrodynamic Atomization", *Med. Eng. Phys.*, 29(7): 749-754 (2007).
Fenster, et al., "Three-dimensional ultrasound imaging", *Phys Med Biol*, 46(5):R67-R99 (2001).
Feshitan et al., "Microbubble Size Isolation by Differential Centrifugation", *Journal of Colloid and Interface Science*, 329: 316-324 (2009).
Fiske, et al., "Special Focus Section: Gene Therapy for Parkinson's Disease", *Experimental Neurology*, 209:28-29 (2008).
Fry, "Transkull Transmission of an Intense Focused Ultrasonic Beam", *Ultrasound in Medicine & Biology*, 3, p. 179 (1977).
Fry, et al., "A Focused Ultrasound System for Tissue Volume Ablation in Deep Seated Brain Sites", *IEEE 1986 Ultrasonics Symposium*, pp. 1001-1004 (1986).
Fujii, et al., "A new method for attenuation coefficient measurement in the liver", *Journal of Ultrasound Medicine*, 21(7):783-788 (2002).
Fung, (1993). Biomechanics—Mechanical Properties of Living Tissues. New York. Table of Contents.
Ganan-Calvo, et al., "Perfectly Monodisperse Microbubbling by Capillary Flow Focusing", *Phys. Rev. Lett.*, 87(27) Pt 1: 274501-1-274501-4 (2001).
Gaud et al., "Acoustic Characterization of Single Ultrasound Contrast Agent Microbubbles", *The Journal of the Acoustic Society of America*, 124(6): 4091 (2008).
Ghosh, et al., "Cardiac Memory in Patients With Wolff-Parkinson-White Syndrome: Noninvasive Imaging of Activation and Repolarization Before and After Catheter Ablation", *Circulation*, 118:907-915 (2008).

Giacobini, "Alzheimer Disease, From Molecular Biology to Therapy", *Advances in Experimental Medicine and Biology*, 429:235-245 (1997).
Ginat, et al., "High-resolution ultrasound elastography of articular cartilage in vitro", Proceedings of the 28th IEEE EMBS Annual International Conference, New York City, USApp. 6644-6647 (Aug. 30-Sep. 3, 2006).
Greenstein, et al., "Mechanisms of Excitation-Contraction Coupling in an Integrative Model of the Cardiac Ventricular Myocyte", *Biophysical Journal*, 90:77-91 (2006).
Greenwald, "Pulse Pressure and Arterial Elasticity", *Qjm—an International Journal of Medicine*, 95(2): 107-112 (2002).
Gupta, et al., "Changes in Passive Mechanical Stiffness of Myocardial Tissue with Aneurysm Formation", *Circulation*, 89:2315-2326 (1994).
Gurev, et al., "Distribution of Electromechanical Delay in the Heart: Insights From a Three-Dimensional Electromechanical Model", *Biophysical Journal*, 99:745-754 (2010).
Gurev, et al., "In Silico Characterization of Ventricular Activation Pattern by Electromechanical Wave Imaging", *Supplement to Heart Rhythm.*, 6:S357 (2009).
Heimdal, et al., "Real-time Strain Rate Imaging of the Left Ventricle by Ultrasound", *J Am Soc EchocardioG*., 11(11): 1013-1019 (1998).
Henderson, et al., "Series Elasticity of Heart Muscle During Hypoxia", *Cardiovascular Research*, 5:10-14 (1971).
Housden, et al., "Ultrasonic imaging of 3D displacement vectors using a simulated 2D array and beamsteering", *Ultrasonics*, 53(2):615-621 (2013).
Huang, et al. "Watershed Segmentation for Breast Tumor in 2-D Sonography", *Ultrasound in Medicine and Biology*, pp. 625-632 (2004).
Hynynen, et al., "Demonstration of Potential Noninvasive Ultrasound Brain Therapy Through an Intact Skull", *Ultrasound in Medicine & Biology*, 24(2): 275-283 (1998).
Hynynen, et al., "Noninvasive MR Imaging—Guided Focal Opening of the Blood-Brain Barrier in Rabbits", *Radiology*, 220(3): 640-646 (2001).
Hynynen, et al., "Trans-Skull Ultrasound Therapy: the Feasibility of Using Image-Derived Skull Thickness Information to Correct the Phase Distortion", *IEEE Transactions on Ultrasonics, Ferroelectrics and Frequency Control*, 46(3): 752-755, (1999).
Hynynen, et al., "Focal Disruption of the Blood-Brain Barrier Due to 260-Khz Ultrasound Bursts: A Method for Molecular Imaging and Targeted Drug Delivery", *J. Neurosurg.*, 105(3): 445-454 (2006).
International Preliminary Report on Patentability, dated Apr. 17, 2007 and Written Opinion for PCT/US2005/037669, dated Jun. 13, 2006.
International Preliminary Report on Patentability, dated Apr. 17, 2007 and Written Opinion for PCT/US2005/037670, dated Nov. 22, 2006.
International Preliminary Report on Patentability, dated Jun. 11, 2008 and Written Opinion for PCT/US2006/061809, dated Oct. 4, 2007.
International Preliminary Report on Patentability, dated Nov. 14, 2007 and Written Opinion for PCT/US2006/018454, dated Aug. 9, 2007.
International Search Report and Written Opinion for PCT/US2006/036460, dated Sep. 5, 2007; International Preliminary Report dated Mar. 26, 2008.
International Search Report and Written Opinion for PCT/US2009/056513, dated Oct. 30, 2009.
International Search Report and Written Opinion for PCT/US2009/052563 dated Oct. 8, 2009.
International Search Report and Written Opinion for PCT/US2009/056565 dated Nov.. 2, 2009.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2011/034704, dated Aug. 18, 2011.

(56) References Cited

OTHER PUBLICATIONS

International Search Report for PCT/US2007/019149 dated Feb. 29, 2008.
Jagannathan, et al., "High-Intensity Focused Ultrasound Surgery of the Brain: Part 1—A Historical Perspective With Modern Applications", *Neurosurgery*, 64(2): 201-211 (2009).
Jasaityte, et al., "Current state of three-dimensional myocardial strain estimation using echocardiography", *J Am Soc Echocardiogr.*, 26(1):15-28 (2013).
Jensen, et al., "Calculation of Pressure Fields From Arbitrarily Shaped, Apodized, and Excited Ultrasound Transducers", *IEEE Transactions on Ultrasonics, Ferroelectrics and Frequency Control*, 39(2): 262-267 (1992).
Kallel, et al., "A Least-Squares Strain Estimator for Elastography", *Ultrasonic Imaging*, 19:195-208 (1997).
Kanai, et al. "Propagation of Spontaneously Actuated Pulsive Vibration in Human Heart Wall and In Vivo Viscoelasticity Estimation", *IEEE Transactions on Ultrasonics, Ferroelectrics, and Frequency Control*, 52(11): 1931-1942 (2005).
Kanai, et al., "A New Method for Measuring Small Local Vibrations in the Heart Using Ultrasound", *IEEE Transactions on Biomedical Engineering*, 40(12): 1233-1242 (1993).
Kanai, et al., "Myocardial Rapid Velocity Distribution", Ultrasound Med Biol., 27(4): 481-498 (2001).
Kanai, et al., "Transcutaneous Measurement of Frequency Dispersion in the Regional Pulse Wave Velocity", *2000 IEEE Ultrasonics Symposium*, pp. 1-4 (2000).
Kaufman, et al., "Ultrasound Simulation in Bone," *IEEE Transactions on Ultrasonics Ferroelectrics and Frequency Control*, 55(6): 1205-1218 (2008).
Kimber, et al., "A Comparison of Unipolar and Bipolar Electrodes During Cardiac Mapping Studies", *Pacing Clin Electro.*, 19:1196-1204 (1996).
Kinoshita, et al., "Noninvasive Localized Delivery of Herceptin to the Mouse Brain by MRI-Guided Focused Ultrasound-Induced Blood-Brain Barrier Disruption", *Proceedings of the National Academy of Sciences*, 103(31): 11719-11723 (2006).
Kinoshita, et al., "Targeted Delivery of Antibodies Through the Blood—Brain Barrier by MRI-Guided Focused Ultrasound", Biochemical and Biophysical Research Communications, 340:1085-1090 (2006).
Klein, et al., "Interdependency of Local Capillary Density, Blood Flow, and Metabolism in Rat Brains", *Amer. J. Physiol.*, 251(6) Pt 2: H1333-H1340 (1986).
Klempner, et al., "Neutrophil Plasma Membranes I. High-Yield Purification of Human Neutrophil Plasma Membrane Vesicles by Nitrogen Cavitation and Differential Centrifugation", *Journal of Cell Biology*, 86:21-28 (1980).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Konofagou, et al. "Elastographic Imaging of the Strain Distribution at the Anterior Cruciate Ligament and ACL-Bone Insertions", *Proceedings of the 2005 IEEE 27th Annual International Conference of the Engineering in Medicine and Biology Society*, pp. 972-975 (Shanghai, China Sep. 1-4, 2005).
Konofagou, et al., "Ultrasound-Induced Blood-Brain Barrier Opening", Current Pharmaceutical Biotechnology, 13(7):1332-1345 (2012).
Konofagou, et al., "A New Elastographic Method for Estimation and Imaging of Lateral Strains, Corrected Axial Strains and Poison's Ratios in Tissues", Ultrasound in Medicine and Biology, 24(8):1183-1199 (1998).
Konofagou, et al., "Mechanism and Safety at the Threshold of the Blood-Brain Barrier Opening In Vivo", *International Society on Therapeutic Ultrasound (ISTU)*, Aix-en-Provence, France, Sep. 21-24, 2009.
Konofagou, et al., "Myocardial Elastography—Feasibility Study in Vivo", *Ultrasound Med & Biol.*, 28(4):475-482 (2002).
Konofagou, et al., "Noninvasive electromechanical wave imaging and conduction-relevant velocity estimation in vivo", *Ultrasonics*, 50(2):208-215 (2010).
Konofagou, et al., "Noninvasive Electromechanical Wave Imaging and Conduction Velocity Estimation In Vivo", *2007 IEEE Ultrasonics Symposium*, pp. 969-972 (2007).
Konofagou, et al., "Three-Dimensional Motion Estimation in Elastography", *IEEE Proceedings of the Symposium of Ultrasonics, Ferroelectrics and Frequency Control in Sendai, Japan*, pp. 1745-1748 (1998).
Korecka, et al., "Cell-Replacement and Gene-Therapy Strategies for Parkinson's and Alzheimers Disease", *Regen. Med.*, 2(4): 425-446 (2007).
Kremkau, et al., "Ultrasonic Attenuation and Propagation Speed in Normal Human Brain", *The Journal of the Acoustical Society of America*, 70:29 (1981).
Kunz, et al., "The Finite Difference Time Domain Method for Electromagnetics," *CRC Press*, Boca Raton, USA (1993).
Kvale, et al., "Size Fractionation of Gas-Filled Microspheres by Flotation", Separations Technol., 6(4): 219-226 (1996).
Lai, et al., "Introduction to Continuum Mechanics" (Pergamon Pr). 3rd Ed. (1993).
Lee, et al., "Improving Stereotactic Surgery Using 3-D Reconstruction", *IEEE Engineering in Medicine and Biology Magazine*, 21:109-116 (2002).
Lee, et al., "Theoretical Quality Assessment of Myocardial Elastography With in Vivo Validation", *IEEE Transactions, Ultrasonics, Ferroelectrics and Frequency Control*, 54:2233-2245 (2007).
Liu, et al., "Hemorrhage Detection During Focused-Ultrasound Induced Blood-Brain-Barrier Opening by Using Susceptibility-Weighted Magnetic Resonance Imaging",*Ultrasound in Med. & Biol.*, 34(4): 598-606 (2008).
Liu, et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage", *J. of Magnetic Resonance Imaging*, 29:31-38 (2009).
Lu, et al., "Design and Experiment of 256-Element Ultrasound Phased Array for Noninvasive Focused Ultrasound Surgery", *Ultrasonics*, 44:e325-e330 (2006).
Luo, et al., "A Fast Normalized Cross-Correlation Method for Motion Estimation", *IEEE Transactions, Ultrasonics, Ferroelectrics and Frequency Control*, 57(6): 1347-1357 (2010).
Luo, et al., "High-Frame Rate, Full-View Myocardial Elastography With Automated Contour Tracking in Murine Left Ventricles In Vivo", *IEEE Transactions, Ultrasonics, Ferroelectrics and Frequency Control*, 55(1): 240-248 (2008).
Luo, et al., "Myocardial Elastography At Both High Temporal and Spatial Resolution for The Detection of Infarcts", *Ultrasound Med. Biol.*, 33(8): 1206-1223 (2007).
Luo, et al., "Pulse Wave Imaging of Normal and Aneurysmal Abdominal Aortas In Vivo", *IEEE Trans. Med. Imaging*, 28(4): 477-486 (2009).
Maleke, et al., "In Vivo Feasibility of Real-Time Monitoring of Focused Ultrasound.Surgery (FUS) Using Harmonic Motion Imaging (HMI)", *IEEE Trans. Biomed. Eng.*, 57(1): 7-11 (2010).
Maleke, et al., "Single-Element Focused Ultrasound Transducer Method for Harmonic Motion Imaging", *Ultrasonic Imaging*, 28(3): 144-158 (2006).
Marquet, et al., "Non-Invasive Transcranial Ultrasound Therapy Based on a 3D CT Scan: Protocol Validation and In Vitro Results", *Phys. Med. Biol.*, 54:2597-2613 (2009).
Mazziotta, et al., "A Probabilistic Atlas of the Human Brain: Theory and Rationale for Its Development the International Consortium for Brain Mapping (ICBM)", *Neuroimage*, 2:89-101 (1995).
McDannold, et al., "Targeted Disruption of the Blood-Brain Barrier With Focused Ultrasound: Association With Cavitations Activity", *Physics in Medicine and Biology*, 51:793-808 (2006).
McDannold, et al., "Use of Ultrasound Pulses Combined With Definity for Targeted Blood-Brain Barrier Disruption: A Feasibility Study", *Ultrasound in Medicine & Biology*, 33(4): 584-590 (2007).

(56) References Cited

OTHER PUBLICATIONS

McDannold, et al., "Blood-Brain Barrier Disruption Induced by Focused Ultrasound and Circulating Preformed Microbubbles Appears to be Characterized by the Mechanical Index", *Ultrasound Med Biol.*, 34(5):834-840 (2008).

McDannold, et al., "MRI-Guided Targeted Blood-Brain Barrier Disruption With Focused.Ultrasound: Histological Findings in Rabbits", *Ultrasound Med. Biol.*, 31(11): 1527-1537 (2005).

McLaughlin, et al., "Piezoelectric Sensor Determination of Arterial Pulse Wave Velocity", *Physiol Meas.*, 24(3): 693-702 (2003).

McNally, et al., "Computer Vision Elastography: Speckle Adaptive Motion Estimation for Elastography Using Ultrasound Sequences", *IEEE Transactions on Medical Imaging*, 24(6):755-766 (2005).

Melodelima, et al., "Thermal Ablation by High-Intensity-Focused Ultrasound Using a Toroid Transducer Increases the Coagulated Volume. Results of Animal Experiments", *Ultrasound in Medicine & Biology*, 35(3): 425-435 (2009).

Mitri, et al., "Chirp Imaging Vibro-Acoustography for Removing the Ultrasound Standing Wave Artifact", *IEEE Transactions on Medical Imaging*, 24(10): 1249-1255 (2005).

Mychaskiw, et al., "Optison (FS069) Disrupts the Blood-Brain Barrier in Rats", *Anesthesia & Analgesia*, 91:798 (2000).

Nichols, et al., "Vascular Impedance. In McDonald's: Blood Flow in Arteries: Theoretical, Experimental and Clinical Principles", E. Arnold. London, *Oxford University Press*, Table of Contents (1998).

Ohtani, et al., "Transmural Ultrasound-Based Visualization of Patterns of Action Potential Wave Propagation in Cardiac Tissue", Annals Biomedical Engineering, 38(10):3112-3123 (2010).

Ophir, et al., "Elastography: A Quantitative Method for Imaging the Elasticity of Biological Tissues", *Ultrasonic Imaging*, 3(2): 111-134 (1991).

Otani, "Use of ultrasound imaging to map propagating action potential waves in the heart", *Computers in Cardiology*, 36:617-620 (2009).

Palmeri, et al., "Characterizing acoustic attenuation of homogeneous media using focused impulsive acoustic radiation force", *Ultrason Imaging*, 28(2):114-128 (2006).

Papadakis, Emmauel P., "Ultrasonic Instruments & Devices", Academic Press, 8 pages (1999).

Pardridge, "Drug Targeting to the Brain", *Pharmaceutical Research*, 24:1733-1744 (2007).

Pardridge, "The Blood-Brain Barrier: Bottleneck in Brain Drug Development", *NeuroRx*, 2:3-14 (2005).

Patel, et al., "GDNF Delivery for Parkinson's Disease", *ACTA Neurochirurgica-Supplementum*, 97(2): 135-154 (2007).

Pernot, et al., "ECG-Gated, Mechanical and Electromechanical Wave Imaging of Cardiovascular Tissues In Vivo", *Ultrasound in Medicine & Biology*, 33(7):1075-1085 (2007).

Pernot, et al., "Electromechanical Imaging of the Myocardium at Normal and Pathological States", *2005 IEEE Ultrasonics Symposium*, pp. 1091-1094 (2005).

Philippens, "Non-Human Primate Models for Parkinson's Disease", *Drug Discovery Today: Disease Models*, 5:105-111 (2008).

Pichardo, et al., "Multi Frequency Characterization of Speed of Sound for Longitudinal Transmission on Freshly Excised Human Skulls" *9th International Society on Therapeutic Ultrasound*, p. 136 (2009.).

Prinzen, et al., "The Time Sequence of Electrical and Mechanical Activation During Spontaneous Beating and Ectopic Stimulation", *Eur. Heart J.*, 13:535-543 (1992).

Provost, et al., "Electromechanical Wave Imaging of Normal and Ischemic Hearts In Vivo", *IEEE Trans. Med. Imaging*, 29:625-635 (2010).

Provost, et al., "Imaging the electromechanical activity of the heart in vivo", *PNAS*, 108(21):8565-8570 (2011).

Provost, et al., "Mapping of cardiac electrical activation with electromechanical wave imaging: An in silico—in vivo reciprocity study", *Heart Rhythm.*, 8(5):752-759 (2011).

Qin, et al., "Acoustic Response of Compliable Microvessels Containing Ultrasound Contrast Agents", *Phys. Med. Biol.*, 51:5065-5088 (2006).

Qin, et al., "The Natural Frequency of Nonlinear Oscillation of Ultrasound Contrast Agents in Microvessels", *Ultrasound in Med. & Biol.*, 33(7):1140-1148 (2007).

Ramanathan, et al., "Activation and Repolarization of the Normal Human Heart Under Complete Physiological Conditions", *Proceedings of the National Academy of Sciences*, 103:6309-6314 (2006).

Ramanathan, et al., "Noninvasive Electrocardiographic Imaging for Cardiac Electrophysiology and Arrhythmia", *Nat Med.*, 10:422-428 (2004).

Raymond, et al., "Ultrasound Enhanced Delivery of Molecular Imaging and Therapeutic Agents in Alzheimer's Disease Mouse Models", *PLoS One*, 3(5):e2175 (2008).

Rice, et al., "Approximate Model of Cooperative Activation and Crossbridge Cycling in Cardiac Muscle Using Ordinary Differential Equations", *Biophys. J.*, 95:2368-2390 (2008).

Rockenstein, et al., "Transgenic Animal Models of Neurodegenerative Diseases and Their Application to Treatment Development", *Adv. Drug Del. Rev.*, 59(11):1093-1102 (2007).

Rogers, et al., "Age-Associated Changes in Regional Aortic Pulse Wave Velocity", *J Am Coll Cardiol.*, 38(4):1123-1129 (2001).

Roth, "Influence of a Perfusing Bath on the Foot of the Cardiac Action Potential", *Circulation Research*, 86:E19-E22 (2000).

Sabraoui, et al., "Feedback Loop Process to Control Acoustic Cavitation", *Ultrasonics Sonochemistry*, 18(2):589-594 (2011).

Samuel, et al., "An Ex Vivo Study of the Correlation Between Acoustic Emission and Microvascular Damage", *Ultrasound Med. Biol.*, 35(9):1574-1586 (2009).

Sanberg, et al., "Brief Communication: Neural Transplants Disrupt the Blood-Brain Barrier and Allow Peripherally Acting Drugs to Exert a Centrally Mediated Behavioral Effect", *Experimental Neurology*, 102:149-152 (1988).

Sandrin, et al., "Time-Resolved Pulsed Elastography with Ultrafast Ultrasonic Imaging", *Ultrason. Imaging*, 21(4): 259-72 (1999).

Sarvazyan, et al., "Shear Wave Elasticity Imaging: A New Ultrasonic Technology of Medical Diagnostics", *Ultrasound Med Biol.*, 24(9): 1419-1435 (1998).

Sassaroli, et al., "Cavitation Threshold of Microbubbles in Gel Tunnels by Focused Ultrasound", *Ultrasound in Med. & Biol.*, 33(10):1651-1660 (2007).

Sassaroli, et al., "Forced Linear Oscillations of Microbubbles in Blood Capillaries", *J. Acoust. Soc. Am.*, 115(6):3235-3243 (2004).

Sassaroli, et al., "Resonance Frequency of Microbubbles in Small Blood Vessels: a Numerical Study", *Phys. Med. Biol.*, 50:5293-5305 (2005).

Schenk, et al., "Immunization With Amyloid-Beta Attenuates Alzheimer-Disease-Like Pathology in The PDAPP Mouse", *Nature*, 400:173-177 (1999).

Scher, et al., "The Pathway of Ventricular Depolarization in the Dog", *Circ Res.*, 4:461-469 (1956).

Schilling, et al., "Simultaneous Endocardial Mapping in the Human Left Ventricle Using A Noncontact Catheter: Comparison of Contact and Reconstructed Electrograms During Sinus Rhythm", *Circulation*, 98:887-98 (1998).

Sengupta, et al., "Electromechanical Activation Sequence in Normal Heart", *Heart Fail Clin.*, 4:303-314 (2008).

Shehata, et al., "Myocardial Tissue Tagging With Cardiovascular Magnetic Resonance", *Journal of Cardiovascular Magnetic Resonance*, 11:55 (2009).

Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", *Ultrasound Med. Biol.*, 32(9): 1399-1409 (2006).

Sheikov, et al., "Cellular Mechanisms of the Blood-Brain Barrier Opening Induced by Ultrasound in Presence of Microbubbles", *Ultrasound Med. Biol.*, 30(7): 979-989.

Sheikov, et al., "Effect of Focused Ultrasound Applied With an Ultrasound Contrast Agent on the Tight Junctional Integrity of the Brain Microvascular Endothelium", *Ultrasound Med. Biol.*, 34(7): 1093-1104 (2008).

(56) References Cited

OTHER PUBLICATIONS

Shinna, et al., "Realtime tissue elasticity imaging using the combined autocorrelation method", *J. Med. Ultrasonics*, 29(autumn):119-128 (2002).
Siegel, et al., "Neurotrophic Factors in Alzheimer's and Parkinson's Disease Brain", *Brain Research Reviews*, 33:199-227 (2000).
Silva, "Nanotechnology Approaches to Crossing the Blood-Brain Barrier and Drug Delivery to the CNS", *BMC Neruosci.*, 9(Suppl 3): S4 (2008).
Sinkus, et al., "High-Resolution Tensor MR Elastography for Breast Tumour Detection", *Phys Med Biol.*, 45(6): 1649-1664 (2000).
Sirsi, et al., "Effect of Microbubble Size on Fundamental Mode High Frequency Ultrasound Imaging in Mice", *Ultrasound in Med. & Bio.*, 36(6): 935-948 (2010).
Spach, et al., "Extracellular Discontinuities in Cardiac Muscle—Evidence for Capillary Effects on the Action Potential Foot", *Circulation Research*, 83:1144-1164 (1998).
Stewart, et al., "Blood-Eye Barriers in the Rat: Correlation of Ultrastructure With Function", *J. Comp. Neurol.*, 340(4): 566-576 (1994).
Stieger, et al., "Enhancement of Vascular Permeability With Low-Frequency Contrast-Enhanced Ultrasound in the Chorioallantoic Membrane Model", *Radiology*, 243(1):112-121 (2007).
Styner, et al., "Automatic Brain Segmentation in Rhesus Monkeys" *2007 Medical Imaging, Proc. of SPIE*, 6512:65122L-1-65122L-8 (2007).
Sutherland, "Color Doppler Myocardial Imaging—Potential Applications in Acquired and Congenital Heart-Disease", *Acta Paediatr.*, 84:40-48 (1995).
Sykova, et al., "Diffusion in Brain Extracellular Space", *Physiol. Rev.*, 88(4): 1277-1340.
Talu, et al., "Tailoring the Size Distribution of Ultrasound Contrast Agents: Possible Method for Improving Sensitivity in Molecular Imaging" *Mol. Imag.*, 6(6): 384-392.
Tang, et al., "Standing-Wave Suppression for Transcranial Ultrasound by Random Modulation", *IEEE transactions on Biomedical Engineering*, 57(1):203-205 (2010).
Tanter, et al., "Focusing and Steering Through Absorbing and Aberrating Layers: Application to Ultrasonic Propagation Through the Skull", *The Journal of the Acoustical Society of America*, 103:2403-2410 (1998).
Tanter, et al., "Ultrafast Compound Imaging for 2-D Motion Vector Estimation: Application to Transient Elastography", *IEEE Trans Ultrason Ferroelectr Freq Control*, 49(10): 1363-74 (2002).
Tavarozzi, et al., "Magnetocardiography: Current Status and Perspectives Part II: Clinical Applications", *Ital Heart J.*, 3:151-165 (2002).
Techavipoo, et al., "Temperature dependence of ultrasonic propagation speed and attenuation in excised canine liver tissue measured using transmitted and reflected pulses", *The Journal of Acoustical Society of America*, 115(6):2859-2865 (2004).
Treat, et al., "Targeted Delivery of Doxorubicin to the Rat Brain at Therapeutic Levels Using MRI-Guided Focused Ultrasound", *Int. J. Cancer*, 121(4): 901-907 (2007).
Tung, et al., "Feasibility of Noninvasive Cavitation-Guided Blood-Brain Barrier Opening Using Focused Ultrasound and Microbubbles in Nonhuman Primates", *Applied Physics Letters*, 98(16):163704 (2001).
Tung, et al., "Identifying the Inertial Cavitation Threshold and Skull Effects in a Vessel Phantom Using Focused Ultrasound and Microbubbles", *Ultrasound in Medicine & Biology*, 36(5): 840-852 (2010).
Tung, et al., "Identifying the Inertial Cavitation Threshold in a Vessel Phantom Using Focused Ultrasound and Microbubbles", *The Journal of the Acoustical Society of America*, 124:2486 (2008).
Tung, et al., "Noninvasive in Vivo Cavitation Threshold Detection During Blood-Brain Barrier Opening Using Focused Ultrasound and the Contrast Agent and Definity", *Joint 159th Meeting of the Acoustic Society of America*, (Apr. 19, 2010).

Tuszynski, et al., "A Phase 1 Clinical Trial of Nerve Growth Factor Gene Therapy for Alzheimer Disease", *Nature Medicine*, 11:551-555 (2005).
Tuszynski, et al., "Nerve Growth Factor Gene Therapy in Alzheimer Disease" *Alzheimer Disease & Associated Disorders*, 21:179-189 (2007).
Unger, E.C. et al., "Therapeutic Applications of Lipid-Coated Microbubbles", *Advanced Drug Delivery Reviews*, 56(9): 1291-1314 (2004).
Vappou, et al., "Quantitative Viscoelastic Parameters Measured by Harmonic Motion Imaging", *Phys. Med. Biol.*, 54:3579-3595 (2009).
Walker, et al., "A Fundamental Limit on Delay Estimation Using Partially Correlated Speckle Signals", *IEEE Transactions, Ultrasonics, Ferroelectrics and Frequency Control*, 42(2): 301-308 (1995).
Walker, et al., "A Fundamental Limit on the Performance of Correlation Based Phase Correction and Flow Estimation Techniques", *IEEE Transactions, Ultrasonics, Ferroelectrics and Frequency Control*, 41(5): 644-654 (1994).
Wang et al., "Qualitative and Quantitative Analysis of the Molecular Delivery Through the Ultrasound-Enhanced Blood-Brain Barrier Opening in the Murine Brain," presented at the *IEEE Symp. Ultrason. Ferroelectr. Freq. Control*, Beijing, China, 2008.
Wang, et al., "A Composite Imaging Technique for High Frame-Rate and Full-View Cardiovascular Ultrasound and Elasticity Imaging", *IEEE Transactions, Ultrasonics, Ferroelectrics and Frequency Control*, 55(10): 2221-2233 (2008).
Wang, et al., "A Composite Imaging Technique for High Frame-Rate and Full-View Cardiovascular Ultrasound and Elasticity Imaging", *IEEE International Ultrasonics Symposium*, New York, NY, Oct. 28-31, 2007.
Wang, et al., "Increased Aortic Stiffness Assessed by Pulse Wave Velocity in Apolipoprotein E-Deficient Mice", *Am J Physiol Heart Circ Physiol.*, 278(2): H428-34 (2000).
Wenk, "A Primate Model of Alzheimer's Disease", *Behavioural Brain Research*, 57:117-122 (1993).
White, et al., "Longitudinal and Shear Mode Ultrasound Propagation in Human Skull Bone", *Ultrasound in Medicine & Biology*, 32:1085-1096 (2006).
Wyman, et al., "Mapping Propagation of Mechanical Activation in the Paced Heart With MRI Tagging", *Am J Physiol Heart Circ Physiol*, 276:H881-891 (1999).
Xu, et al., "Controllable Gas-Liquid Phase Flow Patterns and Monodisperse Microbubbles in a Microfluidic T-Junction Device", *Appl. Phys. Lett.*, 88(13): 133506-1-133506-3 (2006).
Yin, et al., "A Numerical Study of Transcranial Focused Ultrasound Beam Propagation At Low Frequency", *Physics in Medicine and Biology*, 50:1821-1836 (2005).
Yuh, et. al. "Delivery of Systemic Chemotherapeutic Agent to Tumors by Using Focused Ultrasound: Study in a Murine Model", *Radiology*, 234(2): 431-437 (2005).
Zerhouni, et al., "Human Heart: Tagging with MR Imaging—A Method for Noninvasive Assessment of Myocardial Motion", *Radiology*, 169(1): 59-63 (1988).
Zhang, et al., "Noninvasive Three-Dimensional Electrocardiographic Imaging of Ventricular Activation Sequence",*Am J Physiol Heart Circ Physiol.*, 289:H2724-32 (2005).
Zheng, et al. "High Resolution Ultrasound Elastomicroscopy Imaging of Soft Tissues: System Development and Feasibility; Ultrasound Elastomicroscopy", *Physics in Medicine and Biology*, 49(17):3925-3938 (2004).
Zheng, et al., "Ultrasonic measurement of depth-dependent transient behaviors of articular cartilage under compression", Journal of Biomechanics, 38:1830-1837 (2005).
Zheng, et al., "Ultrasound-Driven Microbubble Oscillation and Translation Within Small Phantom Vessels", *Ultrasound Med. Biol.*, 33(12): 1978-1987 (2007).
Zlokovic, "The Blood-Brain Barrier in Health and Chronic Neurodegenerative Disorders", *Neuron*, 57(2): 178-201 (2008).
Zwanenburg, et al., "Timing of Cardiac Contraction in Humans Mapped by High-Temporal-Resolution MRI Tagging: Early Onset and Late Peak of Shortening in Lateral Wall", *Am J Physiol Heart Circ Physiol.*, 286:H1872-1880 (2004).
U.S. Appl. No. 15/165,942, filed May 26, 2016.

(56) References Cited

OTHER PUBLICATIONS

U.S. Appl. No. 14/949,000, filed Nov. 23, 2015, US 2016/0074678, Mar. 17, 2016.
U.S. Appl. No. 13/045,070, Feb. 24, 2016 Issue Fee Payment.
U.S. Appl. No. 13/045,070, Jan. 15, 2016 Notice of Allowance.
U.S. Appl. No. 13/045,070, Jan. 15, 2016 Applicant Initiated Interview Summary.
U.S. Appl. No. 13/045,070, Jan. 7, 2016 Notice of Appeal Filed.
U.S. Appl. No. 13/353,148, Feb. 26, 2016 Notice of Abandonment.
U.S. Appl. No. 13/426,400, Feb. 5, 2016 Notice of Allowance.
U.S. Appl. No. 13/529,239, Jan. 8, 2016 Notice of Abandonment.
U.S. Appl. No. 13/848,436, Jan. 21, 2016 Non-Final Office Action.
U.S. Appl. No. 13/848,436, Dec. 21, 2015 Response to Restriction Requirement.
U.S. Appl. No. 13/848,436, Jul. 22, 2015 Restriction Requirement Filed.
U.S. Appl. No. 14/300,106, Dec. 22, 2015 Issue Fee Payment.
U.S. Appl. No. 14/300,106, Sep. 24, 2015 Notice of Allowance.
Alam et al., "An Adaptive Strain Estimator for Elastography," IEEE Transactions on Ultrasonics, Ferroelectrics, and Frequency Control, vol. 45, No. 2, Mar. 1998, pp. 461-472.
Amin et al., "Therapy planning and monitoring of tissue ablation by high intensity focused ultrasound (HIFU) using imaging and simulation", Conf Proc IEEE Eng Med Biol Soc. 2008, 4471.
International Search Report and Written Opinion dated Jul. 17, 2012 in International Application No. PCT/US12/34136.
International Search Report and Written Opinion dated Oct. 18, 2012 in International Application No. PCT/US12/35685.
Liu et al., "Opening of the Blood-Brain Barrier by Low-Frequency (28-kHz) Ultrasound: A Novel Pinhole-Assisted Mechanical Scanning Device", Ultrasound in Med & Biol., vol. 36, Issue 2, Feb. 2010, pp. 325-335.
Long et al., "An integrated system for therapy planning of high intensity focused ultrasound", Electro/Information Technology, 2008. EIT 2008. IEEE International Conference on May 18-20, 2008, pp. 461-464.
Spalazzi et al., "Elastographic Imaging of Strain Distribution within the Anterior Cruciate Ligament and at the AGL-Bone Insertions," IEEE Ultrasonics Symposium, Sep. 2005, pp. 1755-1758.
Vaezy et al., "Real-time visualization of high-intensity focused ultrasound treatment using ultrasound imaging", Ultrasound Med Biol., Jan. 2001, 27(1), pp. 33-42.
Zheng et al., "A Targeting Method Based on Acoustic Backscatter for Treatment Planning in Tissue Ablation Using Focused Ultrasound", IEEE Trans on Biomed Eng. vol. 57, No. 1, Jan. 2010, pp. 71-79.
Ziadloo et al., "Real-time 3D image-guided HIFU therapy", Conf Proc IEEE Eng Med Biol Soc. 2008, 4459-62.
U.S. Appl. No. 14/476,543, Sep. 22, 2016 Non-Final Office Action.
U.S. Appl. No. 14/091,010, Mar. 13, 2017 Response to Non-Final Office Action.
U.S. Appl. No. 14/091,010, Sep. 12, 2016 Non-Final Office Action.
U.S. Appl. No. 13/848,436, Nov. 1, 2016 Issue Fee Payment.
U.S. Appl. No. 13/848,436, Aug. 2, 2016 Notice of Allowance.
U.S. Appl. No. 13/848,436, Jun. 21, 2016 Response to Non-Final Office Action.
Extended European Search Report dated Jan. 23, 2017 in EP Application No. 10818027.

* cited by examiner

FUS+IV

FUS+IA

SYSTEMS AND METHODS FOR TARGETED DRUG DELIVERY

CROSS-REFERENCE TO RELATED APPLICATIONS

This application claims priority to U.S. Provisional Application Ser. No. 61/864,277, filed Aug. 9, 2013, and U.S. Provisional Application Ser. No. 61/864,285, filed Aug. 9, 2013, each of which is incorporated by reference herein in its entirety.

GRANT INFORMATION

This invention was made with government support under Grant Nos. R01 EB009041, R01 AG038961, R21EB011704, and S10 RR025594, awarded by the National Institutes of Health, Grant No. DMR 1122483 awarded by the National Science Foundation, a NSF Graduate Research fellowship and a grant by the Kinetics Foundation. The U.S. government has certain rights in this invention.

BACKGROUND

The disclosed subject matter relates to systems and methods for targeted drug delivery.

The exchange of molecules across the cerebral microvasculature is regulated by a unique interface known as the blood-brain barrier (BBB). Its primary function is to regulate the brain's environment in order to prevent toxins from entering the parenchyma and maintain molecular environments necessary for proper neuronal firing. The result is the effective exclusion of nearly all systemically administered compounds larger than 400 Da (Daltons) from the brain's extracellular space, rendering many neurologically potent compounds ineffective. So, potential therapeutic agents, such as inhibitors (~1 kDa) and antibodies (30 to 300 kDa), will not reach their intended targets if administered systemically.

Focused ultrasound (FUS) in the presence of systemically administered microbubbles can locally, transiently and reversibly increase the permeability of the BBB, thus allowing targeted delivery of therapeutic agents in the brain for treatment of central nervous system diseases. Exemplary techniques for opening the BBB with FUS are described in U.S. Patent Publication Nos. 2009/0005711, 2011/0295105, 20013/0046229, each of which is incorporated by reference herein in its entirety.

Alternatively, intranasal (IN) drug administration has emerged as a promising approach for drug delivery to the brain. However, when drugs are delivered intranasally, only a small fraction of the drug can reach the CNS from the nasal cavity, which can restrict the application to very potent substances. Furthermore, drugs that are delivered intranasally can be delivered to the whole brain through this route, while neurological diseases do not generally affect the brain in a global manner. Other techniques assume that the microbubbles cross the blood-brain barrier to deliver the drug to the CNS or that the microbubble is injected intranasally.

SUMMARY

The disclosed subject matter provides systems and methods for opening a target tissue and targeted drug delivery using focused ultrasound. In an exemplary embodiment, a method of opening a target tissue using nanodroplets includes targeting a region of the tissue for opening, delivering nanodroplets to the region, and applying an ultrasound beam at the region such that the nanodroplets cavitate, or convert to microbubbles that cavitate, causing the target tissue to open.

In some embodiments, the nanodroplets can have a diameter between 100 nm and 300 nm. In some embodiments the nanodroplets can have a diameter between 150 nm and 250 nm. The ultrasound beam can have a sonication pressure greater than 0.45 MPa. The ultrasound beam can have a sonication pressure greater than 0.6 MPa. Delivering the nanodroplet can includes a least one injection of nanodroplets. The injection can be an intravenous injection or the injection can be an intra-arterial injection. Delivering the nanodroplets and applying the ultrasound beam can be performed simultaneously. The nanodroplets can encapsulate a therapeutic agent In another aspect of the disclosed subject matter, methods of delivering a therapeutic agent through a blood vessel having a BBB to a target location in the brain are provided. In one embodiment, a method can include targeting a region of the blood vessel proximate the target location in the brain, delivering nanodroplets to the region, delivering the therapeutic agent to the region, and applying an ultrasound beam at the region such that the nanodroplets cavitate, or convert to microbubbles causing the BBB to open and allowing the therapeutic agent to diffuse out to the target location in the brain. The conversion to microbubbles can be due to change in pressure and/or temperature.

In some embodiments, the therapeutic agent can be antibodies, neural stem cells, siRNA, chemotherapeutic molecules, adenoviral vectors and neurotrophic factors. The nanodroplet can have a diameter between 100 nm and 300 nm. In some embodiments, the nanodroplet can have a diameter between 150 nm and 250 nm. The ultrasound beam can have a sonication pressure greater than 0.45 MPa. The ultrasound beam can have a sonication pressure greater than 0.6 MPa. The ultrasound beam can have a sonication pressure lower than 0.3 MPa. Delivering the nanodroplets can include a least one injection of nanodroplets. The injection can be an intravenous injection or the injection can be an intra-arterial injection. Delivering the nanodroplets can include delivering the nanodroplets intranasally. Delivering the therapeutic agent can include at least one injection of the therapeutic agent. The injection can be an intravenous injection or the injection can be an intra-arterial injection. Delivering the therapeutic agent can include delivering the therapeutic agent intranasally. Delivering the nanodroplets and applying the ultrasound beam can be performed simultaneously. The nanodroplets can encapsulate a drug.

In another aspect of the disclosed subject matter, methods of delivering a therapeutic agent to a target location in a brain of a patient are provided. In one embodiment, a method can include delivering the therapeutic agent intranasally, targeting a region of a blood vessel proximate the target location in the brain, injecting bubbles into the patient such that the bubbles travel to the region of the blood vessel, and applying an ultrasound beam at the region such that the bubbles cavitate, generating mechanical effects on nearby vessels and tissue and enhancing delivery of the therapeutic agent.

In some embodiments, the bubbles can be microbubbles. The microbubbles can have a median diameter between 1 and 8 μm. The microbubbles can have a median diameter between 4 and 5 μm. In some embodiments the bubbles can be nanodroplets. In some embodiments the mechanical effects can include at least one of high shear stress, microstreaming, and microjeting the blood vessel, thereby allowing transvascular delivery of the therapeutic agent. In some embodiments the mechanical effects can include pushing and pulling surrounding tissue, thereby causing bulk fluid flow in perivascular spaces. The ultrasound beam can include a center frequency of about 1.5 MHz, a peak-negative pressure of about 0.45 MPa, a pulse length of about 6.7 ms, a pulse repetition frequency of about 5 Hz, and a duration of about 1 minute. The therapeutic agent can be disposed at the target location in the brain at a supra-therapeutic level and the therapeutic agent can be disposed elsewhere in the brain at a sub-therapeutic level. Applying the therapeutic agent and applying the ultrasound beam can be performed simultaneously. Applying the ultrasound beam can be performed prior to delivering the therapeutic agent.

In one embodiment, a method can include delivering the therapeutic agent intra-arterially, and targeting a region of a blood vessel proximate the target location in the brain. The method can include injecting a plurality of bubbles into the patient such that the bubbles travel to the region of the blood vessel and applying an ultrasound beam at the region such that the bubbles cavitate thereby generating mechanical effects on the nearby vessels and tissue and enhancing delivery of the therapeutic agent.

In some embodiments, the bubbles can be microbubbles. The microbubbles can have a median diameter between 1 and 8 µm. The microbubbles can have a median diameter between 4 and 5 µm. In some embodiments the bubbles can be nanodroplets. In some embodiments the mechanical effects can include at least one of high shear stress, microstreaming, and microjeting the blood vessel, thereby allowing transvascular delivery of the therapeutic agent. In some embodiments the mechanical effects can include pushing and pulling surrounding tissue, thereby causing bulk fluid flow in perivascular spaces. The ultrasound beam can include a center frequency of about 1.5 MHz, a peak-negative pressure of about 0.45 MPa, a pulse length of about 6.7 ms, a pulse repetition frequency of about 5 Hz, and a duration of about 1 minute. The therapeutic agent can be disposed at the target location in the brain at a supra-therapeutic level and the therapeutic agent can be disposed elsewhere in the brain at a sub-therapeutic level. Applying the therapeutic agent and applying the ultrasound beam can be performed simultaneously. Applying the ultrasound beam can be performed prior to delivering the therapeutic agent.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

The methods and systems presented herein can be used for targeted drug delivery using focused ultrasound (FUS). In some embodiments, acoustically-activated nanodroplets can be used as a contrast agent to mediate FUS-induced blood-brain barrier (BBB) opening. Although the description is focused on the example of opening the BBB, the systems and methods herein are useful for opening other tissues, such as muscular tissue. As used herein, the term bubble can include microbubbles, nanobubbles, and nanodroplets.

Figure 1:
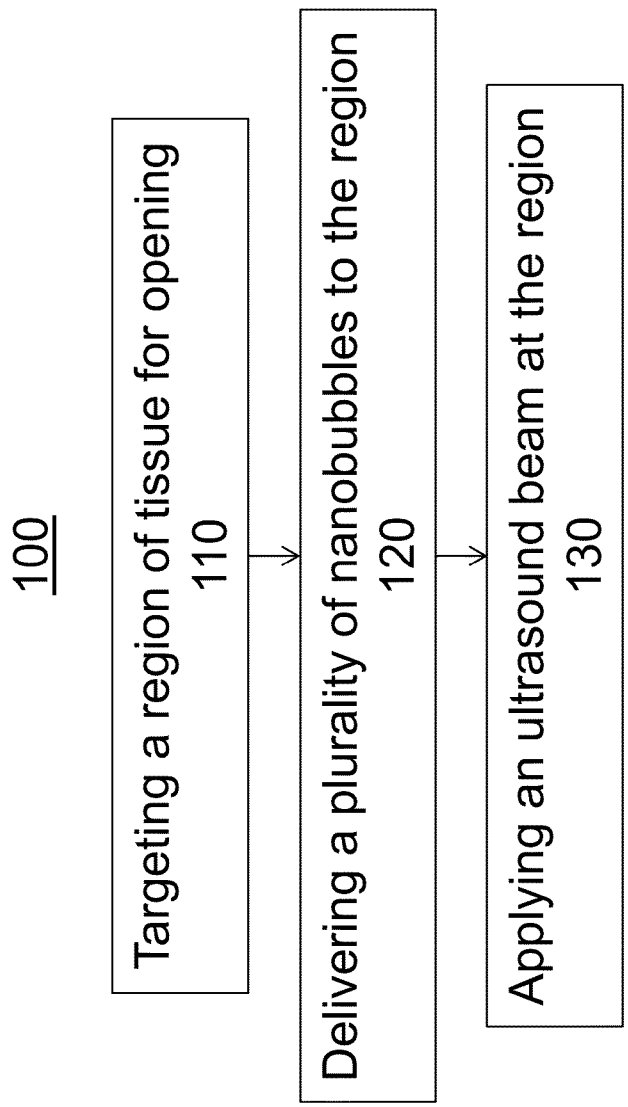
FIG. 1 illustrates a method of opening a target tissue using nanodroplets in accordance with an exemplary embodiment of the disclosed subject matter.

For purpose of illustration and not limitation, FIG. 1 illustrates a method (100) of opening a target tissue using nanodroplets. The tissue can be, for example, a blood vessel having a BBB. The method can include delivering a plurality of nanodroplets to the region (120). The nanodroplets can have a diameter between 100 nm and 300 nm, and in some embodiments, the nanodroplets can each have a diameter between 150 nm and 250 nm. The method can also include delivering an ultrasound beam at the region (130). The ultrasound beam can be a FUS beam. The ultrasound beam can have a sonication pressure greater than 0.45 MPa, and in some embodiments, the ultrasound beam can have a sonication pressure greater than 0.6 MPa. The ultrasound beam can be delivered at the same time the nanodroplets are delivered. Delivering the nanodroplets can include at least one injection of the nanodroplets, for example, into a vein or an artery of the subject. The artery can be, for example, the carotid artery. In some embodiments, the nanodroplets can encapsulate a therapeutic agent. The droplets do not necessarily cross the opening.

Figure 2:
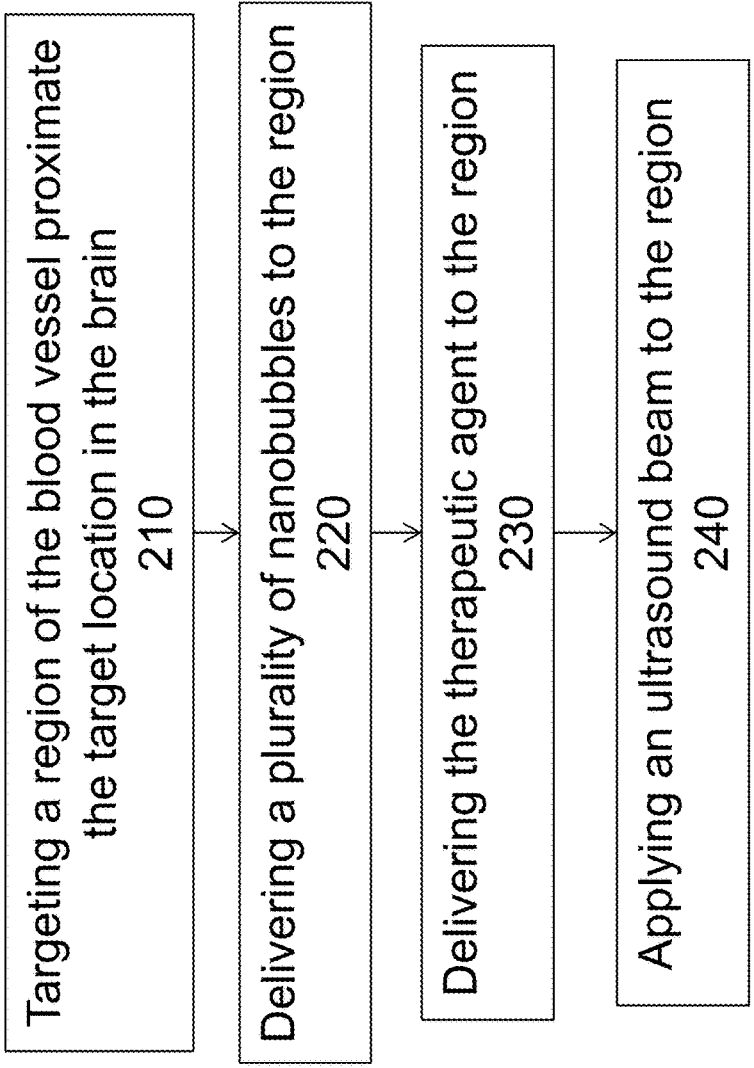
FIG. 2 illustrates a method of delivering a therapeutic agent through a blood vessel having a blood brain barrier to a target location in a brain in accordance with an exemplary embodiment of the disclosed subject matter.

For purpose of illustration and not limitation, FIG. 2 illustrates a method (200) of delivering a therapeutic agent through a blood vessel having a BBB to a target location in a brain. The method can include targeting a region of the blood vessel proximate to the target location in the brain (210). The method can further include delivering a plurality of nanodroplets to the region (220) and delivering the therapeutic agent to the region (230). The method can also include delivering an ultrasound beam to the region (240). The ultrasound beam can be a FUS beam. Applying the ultrasound beam can cause the BBB to open and can allow the therapeutic agent to diffuse out of the blood vessel through the open BBB and to the target location in the brain.

The method can be used for treatment of central nervous system diseases, including Alzheimer's, Huntington's, Parkinson's diseases as well as brain cancers. The therapeutic agent can be one or more of antibodies, neural stem cells, siRNA, chemotherapeutic molecules, and neurotrophic factors. As noted above, the nanodroplets can have a diameter between 100 nm and 300 nm, and in some embodiments, the nanodroplets can each have a diameter between 150 nm and 250 nm. The ultrasound beam can have a sonication pressure greater than 0.45 MPa, and in some embodiments, the ultrasound beam can have a sonication pressure greater than 0.6 MPa. The nanodroplets can be delivered by injection. The therapeutic agent and/or nanodroplets can be delivered by injection or by intranasal delivery.

Figure 3:
FIG. 3 illustrates a method of delivering a therapeutic agent to a target location in a brain of a patient in accordance with an exemplary embodiment of the disclosed subject matter.

Referring to FIG. 3, for the purpose of illustration and not limitation, illustrates a method (300) of delivering a therapeutic agent to a target location in a brain of a patient. The method (300) can include delivering the therapeutic agent (310). In some embodiments, delivering the therapeutic agent (310) can be performed intranasally. In some embodiments, the intranasal delivery can be to the lower two-thirds of the patient's nasal cavity. Alternatively, or additionally, intranasal delivery can be to the upper one-third of the patient's nasal cavity. In some embodiments, delivering the therapeutic agent (310) can be performed intra-arterially. The method (300) can further include targeting a region of the blood vessel proximate the target location in the brain (320). The method can include injecting a plurality of bubbles (330). The bubbles can be injected such that the bubbles travel to the region of the blood vessel. In some embodiments the bubbles can be one or more of microbubbles and nanodroplets. Finally the method can include applying an ultrasound beam (340). The ultrasound beam can be applied at the region such that the bubbles cavitate thereby generating mechanical effects on the nearby vessels and tissue and enhance delivery of the therapeutic agent. The ultrasound beam can include a center frequency of about 1.5 MHz, a peak-negative pressure of about 0.45 MPa, a pulse length of about 6.7 ms, a pulse repetition frequency of about 5 Hz, and a duration of about 1 minute. Delivering the ultrasound beam can be performed simultaneously with the delivery of the therapeutic agent or it can be performed prior to the delivery of the therapeutic agent. In some embodiments, the therapeutic agent can be disposed at the target location in the brain at a supra-therapeutic level and the therapeutic agent is disposed elsewhere in the brain at a sub-therapeutic level.

Cavitation is caused by bubbles passing through the FUS focal region, and is a term for ultrasound-induced activities of bubbles, including their oscillation and/or collapse. Cavitation is usually divided into two classes: stable cavitation (bubbles stably oscillate) and inertial cavitation (bubbles rapidly collapse). The cavitation emissions from bubbles during FUS sonication can be detected, allowing real-time monitoring of the FUS treatment. Cavitation can generate mechanical effects on the nearby blood vessels, such as high shear stress, microstreaming, and microjeting, which can enable transvascular delivery of drugs in the blood circulation. Furthermore, the oscillating bubbles can push and pull on the blood vessels along with surrounding tissues, and can induce expansion and contraction of the perivascular spaces. The movement of the perivascular spaces can induce convective bulk fluid flow, and can enhance drug penetration. The radiation force generated by the FUS itself, without bubbles, can generate shear stress on the tissue and can increase hydraulic conductivity of the interstitial space, which can increase drug diffusion. The mechanical effects of FUS and the cavitating bubbles can contribute to the enhanced brain delivery of intravenously injected therapeutic agents. Similar mechanical effects can also enhance the delivery of drugs administered intranasally.

Example 1

For purpose of illustration and not limitation, acoustically-activated nanodroplets were used as contrast agents to mediate FUS-induced BBB opening in order to study the feasibility of utilizing these nanoscale phase-shift particles for targeted drug delivery in the brain. Significant dextran delivery was achieved in the mouse hippocampus using nanodroplets at clinically relevant pressures. Passive cavitation detection was used in the attempt to establish a correlation between the amount of dextran delivered in the brain and the acoustic emission record during sonication. Conventional microbubbles with the same lipid shell composition and perfluorobutane core as the nanodroplets were also used to compare the efficiency of FUS-induced dextran delivery. It was found that nanodroplets had a higher BBB opening pressure threshold but a lower stable cavitation threshold than microbubbles, suggesting that contrast agent-dependent acoustic emission monitoring would be beneficial. More homogeneous dextran delivery within the targeted hippocampus was achieved using nanodroplets without inducing inertial cavitation or compromising safety.

Initially in the liquid state, nanoscale droplets show high stability in circulation and can be generated in sizes small enough to extravasate through leaky vasculature, and can expand to form microbubbles capable of oscillation in similar fashion as traditional microbubbles when exposed to sufficient rarefactional pressures. Droplet activation can depend on the local rarefactional pressure, and the microbubbles can thus be generated within the narrow focal region where acoustic properties are the strongest. As such, therapeutic effects can be targeted to the desired treatment areas. Once initial BBB permeabilization is achieved, the nanodroplets can be small enough for potential extravasation during subsequent passes through the vasculature. Once entered into the interstitial space behind the barrier, the nanodroplets can then be acoustically activated to form vaporized gaseous bubbles outside the constraints of the cerebral microvessels. An extravascularly activated contrast agent for enhanced drug delivery can be applied at sites that are located deeply in the brain tissue or at regions with relatively low vasculature density. Activation of typical nanodroplet formulations can require acoustic pressures much higher than those used for FUS-induced BBB openings, but nanodroplets can be generated from highly volatile perfluorocarbons by pressurizing preformed microbubbles and condensing the gas core into liquid phase during slow cooling. This methodology can produce uniform nanodroplet size distributions with peak diameters near 200-300 nm that vaporize at acoustic pressures on the order of those required for BBB opening with microbubbles.

Nanodroplets and microbubbles were formulated using the same lipid composition container 90 mol % 1,2-distearoyl-sn-glycero-3-phosphocholine (DSPC) and 10 mol % 1,2-distearoyl-sn-glycero-3-phosphoethanolamine-N-[methoxy(polyethylene glycol)2000] (DSPE-PEG2000) (Avanti Polar Lipids, Alabaster, Ala.). The perfluorobutane gas (PFB, 99 wt % purity) used for contrast agent generation was obtained from FluoroMed (Round Rock, Tex.). All chemicals were used as purchased without further purification.

Microbubbles were generated via mechanical agitation using a Vialmix shaker (Bristol-Myers-Squibb, New York, N.Y.). A Multisizer III particle counter (Beckman Coulter, Opa Locka, Fla.) with a 30 µm aperture was used to measure the microbubble suspension size distribution and concentration.

Nanodroplets were generated via microbubble condensation, in which pre-formed microbubbles of volatile compounds were reverted to the liquid state by application of reduced temperature and increased ambient pressure. PFB microbubbles were generated as described above and allowed to cool to room temperature. The vial containing the microbubbles was then immersed in a $CO_2$/isopropanol bath maintained at a temperature between −7° C. and −10° C. for approximately 1 min. The vial was subsequently connected to an adjustable air-pressure supply, and the headspace pressure inside the microbubble vial increased 30-70 kPa for approximately 30 s to facilitate condensation. A Malvern Nano Zetasizer (Malvern Instruments Ltd., Malvern, Worcestershire, U.K.) was used to measure the size distribution of the droplet emulsion generated.

For purpose of illustration and not limitation, and as embodied herein, an in vitro acoustic nanodroplet vaporization configuration is provided. An ultra-high-speed framing camera with a 24-frame buffer (SIMD24; Specialised Imaging, Simi Valley, Calif.) was interfaced with an inverted microscope (IX71; Olympus, Center Valley, Pa.) with a 100× (NA=1.0) water immersion objective. An acrylic-lined, continuously degassed water bath was mounted to the microscope and maintained at 37° C. The optical resolution of the system allowed observation of particles larger than approximately 500 nm. A 1 MHz spherically-focused piston transducer with a 2.2 cm diameter and a focal length of 3.75 cm (IL0106HP; Valpey Fisher Corp., Hopkinton, Mass.) was aligned with the optical focus by use of a calibrated needle hydrophone (HNA-0400; Onda Corp., Sunnyvale, Calif.). The transducer was driven by sinusoidal 20-cycle pulses generated by a manually-triggered arbitrary waveform generator (AFG 3101; Tektronix, Inc., Beaverton, Oreg.) amplified 60 dB (A500; ENI, Rochester, N.Y.). The sinusoid amplitude was adjusted to change the peak rarefactional pressure experienced by the droplets in focus. The manual trigger was synchronized with the input of the high-speed camera in order to simultaneously capture video of droplet vaporization. Droplet emulsions were diluted 50% in phosphate-buffered saline (PBS) and pumped through a nearly optically and acoustically transparent microcellulose tube (Spectrum Laboratories, Inc., Greensboro, N.C.). The focal plane of the tube was controlled via a 3-axis micropositioner (MMO-203; Narishige Group, East Meadow, N.Y.). The ultra-high-speed camera was set to operate at 20 million frames per second with a 30 ns exposure such that many frames could be captured within a single cycle of the ultrasound pulse. The transducer was calibrated at focus by the needle hydrophone (HNA-0400). A total of 80 male C57BL/6 mice (Harlan Laboratories; Indianapolis, Ind.) weighing 20-25 g were used. The animals were divided into two experimental groups using either nanodroplets (group #1) or microbubbles (group #2) as the contrast agents for FUS-induce BBB opening. The groups were further divided into 14 cohorts based on the experimental protocol as listed in Table 1. Before sonication, each mouse was anesthetized using 1-2% isoflurane-oxygen mixture (SurgiVet, Smiths Medical PM; Norwell, Mass.) and its hair on the scalp was removed with an electric clipper and a depilatory cream. A modified 27-gauge 1½ butterfly catheter (Terumo Medical; Somerset, N.J.) was inserted into the tail vein for contrast agent injection. The animal body temperature was maintained throughout the procedure using a heated pad.

TABLE 1

Summary of the experimental groups.

| | | Number of mice per experimental condition[a] | | | | | |
|---|---|---|---|---|---|---|---|
| | Contrast | | Acoustic pressure (MPa) | | | | |
| Group | Agent | Sham | 0.15 | 0.225 | 0.30 | 0.45 | 0.60 |
| 1 | Nanodroplet | 6 | 6 | 6 | 7 | 7 | 8 |
| 2 | Microbubble | 5 | 7 | 7 | 7 | 7 | 7 |

[a]Number shown including up to 2 mice per experimental condition used for histology examination.

Figure 4:
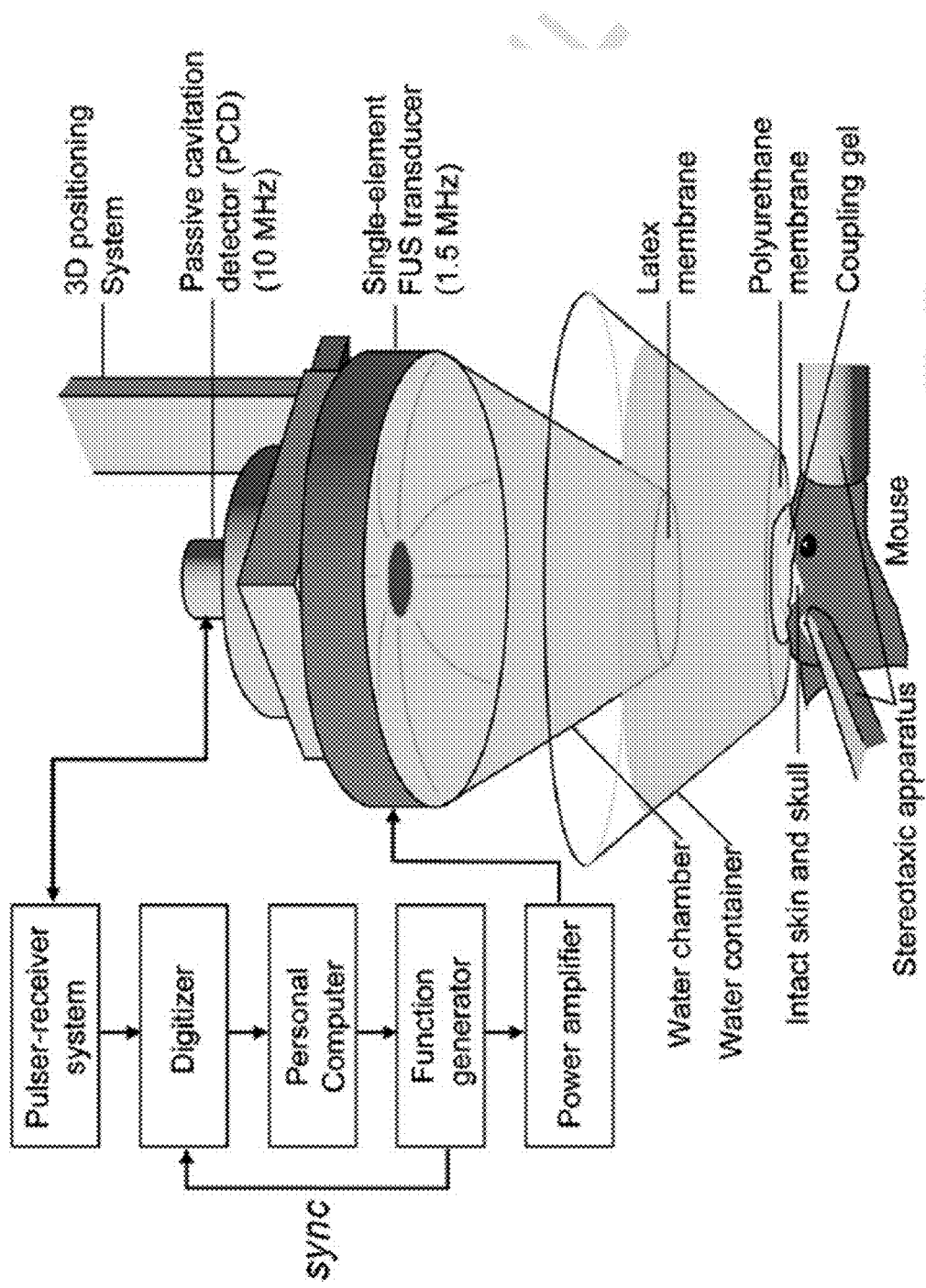
FIG. 4 illustrates a system for opening and/or imaging the opening of a BBB in a brain of a subject in accordance with an exemplary embodiment of the disclosed subject matter.

An exemplary in vivo BBB opening ultrasound setup is illustrated in FIG. 4. A single-element, spherical FUS transducer (center frequency: 1.5 MHz; focal depth: 60 mm; Imasonic, Besancon, France) was driven by a function generator (Agilent Technologies, Palo Alto, Calif.) through a 50 dB power amplifier (E&I, Rochester, N.Y.). A confocal pulse-echo transducer (center frequency: 10 MHz; focal length: 60 mm; Olympus NDT, Waltham, Mass.), which was attached to a computer-controlled 3D positioning system (Velmex, Lachine, QC, Canada), was used to target specific brain structures. The FUS transducer was moved 3 mm laterally of the sagittal suture and 2 mm anterior of the lambdoid suture to target the mouse hippocampus. The pulse-echo transducer, which was driven by a pulser-receiver system with a 20 dB amplification in the receive-only mode (Model 5800; Olympus NDT), was connected to a digitizer (Gage Applied Technologies, Lachine, QC, Canada) to passively acquire acoustic emissions from activated nanodroplets and microbubbles within ±1 V input range.

The pressure amplitude values were corrected to account for 18.1% attenuation through the murine skull, whereas the axial and lateral full-widths at half-maximum intensities of the beam were 7.5 mm and 1 mm, respectively. The acoustic exposure reported throughout the present Example is given in terms of the peak-rarefactional pressure amplitudes.

For purpose of illustration and not limitation, and as embodied herein, an exemplary in vivo BBB opening protocol is provided. Pulsed FUS (pulse length: 0.67 µs; pulse repetition frequency: 5 Hz; duration: 5 min) at acoustic pressures ranging between 0.15 and 0.60 MPa was applied transcranially to the targeted left hippocampus of the mouse brain while the right hippocampus served as the control. Prior to any contrast agent administration, a 30-s sonication using the same acoustic parameters was applied in order to measure the baseline background signal needed in the acoustic emission analysis, as described below. The injected contrast agent samples were freshly diluted before each animal injection. For group #1, a 60 µL nanodroplet suspension was first diluted at 50 vol % using PBS. It was then co-administered, via bolus injection, with 60 µL 3 kDa dextran solution (Life Technologies; Carlsbad, Calif.) at 2 mg/mL concentration through the tail vein 10 s prior to each sonication. For group #2, the microbubble suspension was diluted in PBS to a final concentration of $8\times10^8$ #/mL, and a 60 µL of the diluted microbubble sample, together with 60 µL dextran solution was bolus injected following the same protocol. In addition, two sham cohorts to which no ultrasound was applied were also injected with either nanodroplets or microbubbles and fluorescent dextrans to serve as the basis for comparison in the fluorescence imaging analysis (see description below).

A 1-h period was allowed after sonication to enable the dextran to circulate throughout the vasculature and diffuse into the brain parenchyma. At the end of the allotted time, the animal was sacrificed by transcardiac perfusion using 30 mL PBS for 5 min followed by 60 mL 4% paraformaldehyde for 8 min. The mouse brain was extracted from the skull, post-fixed in 4% paraformaldehyde overnight, and then prepared for either frozen (60 µm) or paraffin (6 µm) sections. The frozen sections were used to analyze fluorescence intensity in order to determine the BBB opening magnitude, while the paraffin sections were used to study the safety of the procedure through histological examinations of representative brain samples from each treatment cohort via hematoxylin and eosin (H&E) staining. The histology image interpretation was performed blindly, i.e., without knowledge of the FUS exposure parameters.

Bright-field and epi-fluorescence images of the brain sections were captured using an Olympus DP30BW digital camera mounted on an upright Olympus BX61 microscope. The extent of BBB opening was determined based on the quantification of dextran delivery into the targeted hippocampus. A section representing the ventral-dorsal midline, as determined by anatomical landmarks, was first selected, and 4 adjacent sections were then selected on either the dorsal or the ventral side of the midline. The sonicated (left) and the control (right) hippocampus was manually outlined using MATLAB (The Mathworks; Natick Mass.), and the spatial average of fluorescence intensity in the region of interest (ROI) was calculated using ImageJ (National Institutes of Health, Bethesda, Md.). The relative fluorescence enhancement was calculated by dividing the difference in fluorescence intensity between the left and right ROIs by the spatial average of the right hippocampus. A fluorescence intensity threshold, defined as twice that of the standard deviation of the control ROI, was applied on each image in order to separate the fluorescence signal from dextran molecules from the background tissue autofluorescence. For each brain, the reported fluorescence enhancement was thus approximated as the sum of the relative fluorescence intensity from all 9 sections. Successful dextran delivery for an individual brain was concluded if the fluorescence enhancement was higher than two standard deviations relative to the average of the corresponding sham cohort. The fluorescence enhancement value for each of the 12 experimental conditions was obtained by averaging all mice sonicated under the same acoustic exposure.

Acoustic emission analysis was performed as described herein. To quantify the acoustic responses of the vaporized nanodroplets or microbubbles, two cavitation parameters were calculated: stable cavitation dose (SCD) and inertial cavitation dose (ICD). The SCD, which was associated with the stable nonlinear oscillation of the contrast agents, was quantified based on the peak amplitude of the spectra around each harmonic frequency of each pulse in the range between 3 and 9 MHz over the first minute sonication duration. The ICD, which was associated with the inertial energy of the collapsing microbubbles, was quantified based on the broadband emission after filtering the harmonic and ultraharmonic signals using a comb filter with rectangular rejection bands centered around the harmonic and ultraharmonic frequencies (rejection bandwidths of 350 kHz and 100 kHz, respectively) across the same frequency range over the same sonication duration. The net emission from the contrast agents could then be determined by subtracting the background signal measured using the same acoustic exposure prior to nanodroplet or microbubble administration.

An unpaired two-tailed Student's t-test was performed to evaluate the significance of the fluorescence enhancement between the sonicated and the control hippocampus under each of the acoustic exposures. In addition, unpaired two-tailed Student's t-tests were used to determine the significance of the acoustic emission responses from the contrast agents across different sonication pressures. All statistical analysis was performed using GraphPad Prism (La Jolla, Calif.).

Figure 5A:
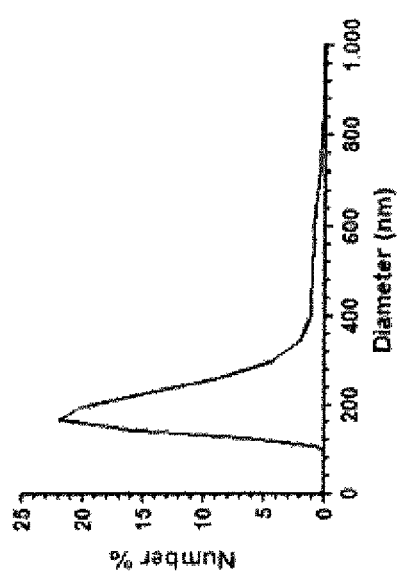
FIGS. 5A and 5B illustrate representative size distributions of nanodroplets and microbubbles, respectively.

The PFB phase-shift nanodroplet emulsions appeared partially translucent by visual inspection. FIG. 5A shows a representative number-weighted size distribution obtained by averaging 3 separate samples (3 measurements per sample). The size distributions measured in the present in vivo study were similar across all samples, and fell within the instrumental uncertainty of the Zetasizer. The averaged number-weighted mean, median and mode diameters across all samples were 204±10 nm, 209±29 nm and 180±25 nm, respectively.

Figure 5B:
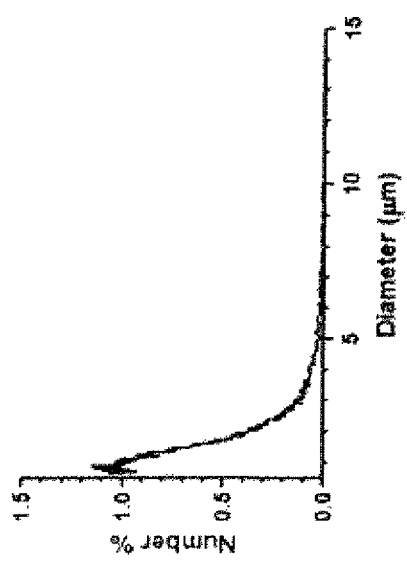

The mechanical agitation method produced opaque milky microbubble suspensions that were stable during the experimental timeframe. FIG. 5B shows a representative number-weighted size distribution of the microbubble sample as measured by Multisizer III. The size distributions among all microbubble suspensions used throughout the study were found to be statistically the same, and the averaged number-weighted mean, median and mode diameters were 1.36±0.32 µm, 1.08±0.23 µm and 0.86±0.35 µm, respectively.

Figure 6:
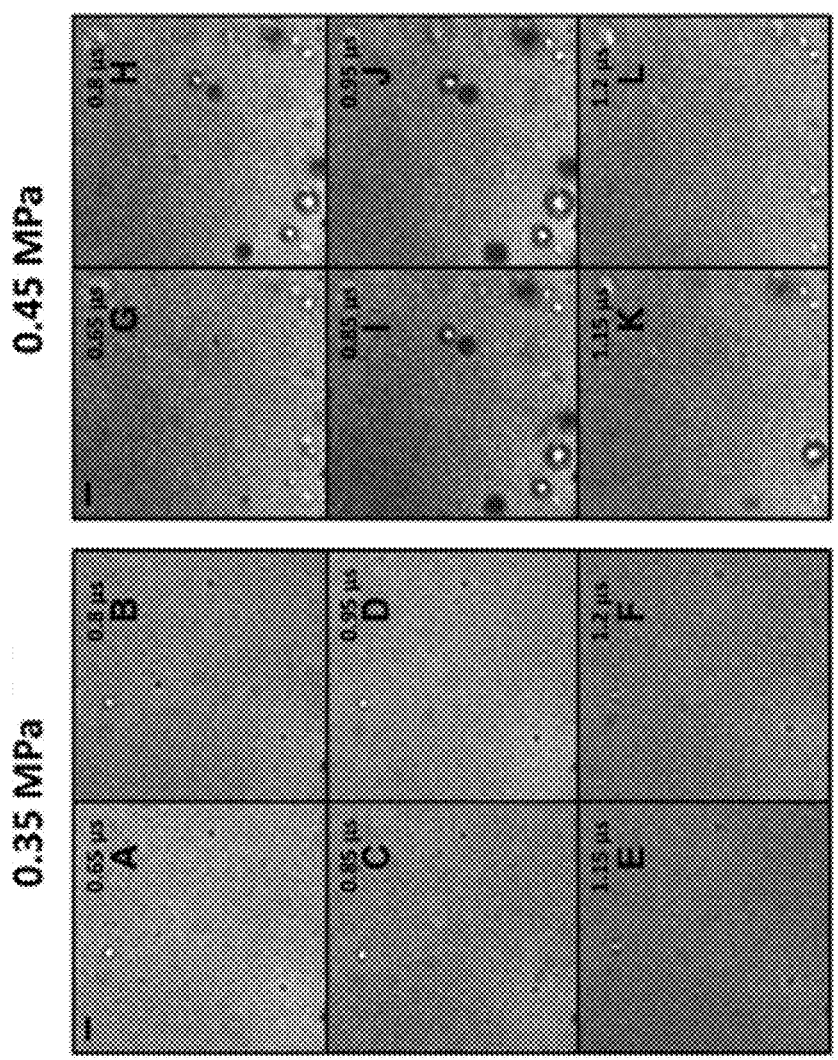
FIG. 6 includes still-frame images depicting nanodroplet activation within the first two cycles of the pulse as a function of sonication pressure.

For purpose of illustration and not limitation, as embodied herein, in vitro acoustic nanodroplet vaporization is provided. To confirm the nanodroplets generated via microbubble condensation were acoustically vaporizable, high-speed optical microscopy was used to visually verify the vaporization of individual stationary droplets at pressures relevant to the in vivo Example. FIG. 6 shows that at peak-rarefactional pressure of approximately 0.35 MPa, no detectable number of vaporized bubbles appeared within the focal plane. However, when the pressure amplitude was increased to 0.45 MPa, vaporized bubbles were observed almost immediately upon exposure to the ultrasound beam. These acoustically activated bubbles were within the micrometer size range and appeared to be acoustically responsive (i.e., they could expand and contract according to the pressure change during a single pulse). The activation of sub-micron droplets was also repeatedly observed at higher pressures (up to 1.1 MPa tested in the current study) using the in vitro setup.

Using fluorescently-labeled 3 kDa dextran as a model drug molecule, the extent of the FUS-induced BBB opening can be quantified as the relative fluorescence enhancement in the sonicated hippocampus over the control. The two sham cohorts, for which no ultrasound was applied, did not show any change in fluorescence intensity between the two hemispheres (images not shown). Quantified fluorescence enhancement results confirmed this observation as no detectable increase in fluorescence intensity between the two ROIs was calculated (Table 2). For the rest of the 12 experimental conditions, the measured fluorescence enhancement was compared to their corresponding sham cohort in order to determine whether sufficient amount of dextran molecules were delivered into the targeted region.

TABLE 2

Summary of the fluorescent imaging analysis.

| Contrast agent | Acoustic Pressure (MPa) | Fluorescence enhancement (%) | Number of mice with significant dextran delivery/Total number of mice evaluated |
|---|---|---|---|
| Nanodroplet | Sham | 21.41 ± 25.97 | 0/6 |
| | 0.15 | 11.04 ± 30.75 | 0/5 |
| | 0.225 | 12.73 ± 38.81 | 0/5 |
| | 0.30 | 18.70 ± 36.07 | 1/6 |
| | 0.45 | 91.84 ± 67.91 | 3/5 |
| | 0.60 | 155.09 ± 55.03 | 7/7 |
| Microbubble | Sham | −7.67 ± 15.41 | 0/5 |
| | 0.15 | 5.95 ± 17.04 | 0/5 |
| | 0.225 | 72.26 ± 114.28 | 3/5 |
| | 0.30 | 184.10 ± 110.77 | 5/5 |
| | 0.45 | 353.64 ± 46.23 | 5/5 |
| | 0.60 | 487.82 ± 271.31 | 5/5 |

Figure 7A:
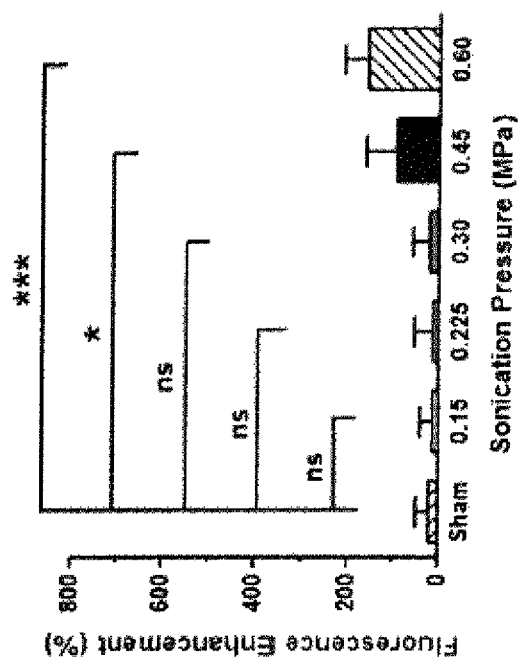
FIGS. 7A and 7B illustrate normalized fluorescence enhancement between the targeted and the control hippocampi using nanodroplets and microbubbles, respectively, to mediate BBB opening at specific sonication pressures.

Following the systemic administration of nanodroplets and subsequent BBB opening, a significant increase in dextran delivery in the targeted ROI was observed at 0.45 and 0.60 MPa (60% opening efficiency with P=0.047 and 100% opening efficiency with P=0.0002, respectively) while only up to 33% of the animals evaluated showed a significant fluorescence enhancement when sonicated at pressures below 0.45 MPa (Table 2). Due to the inconsistency across animals, there was no statistically significant (P>0.56) increase in fluorescence enhancement to clearly indicate BBB opening with dextran delivery for sonication pressures ranging between 0.15 and 0.30 MPa (FIG. 7A). At pressures above 0.45 MPa, fluorescence was observed not only within or near large vessels, but also diffusely distributed across the hippocampi (FIGS. 8D and 8E).

Figure 7B:
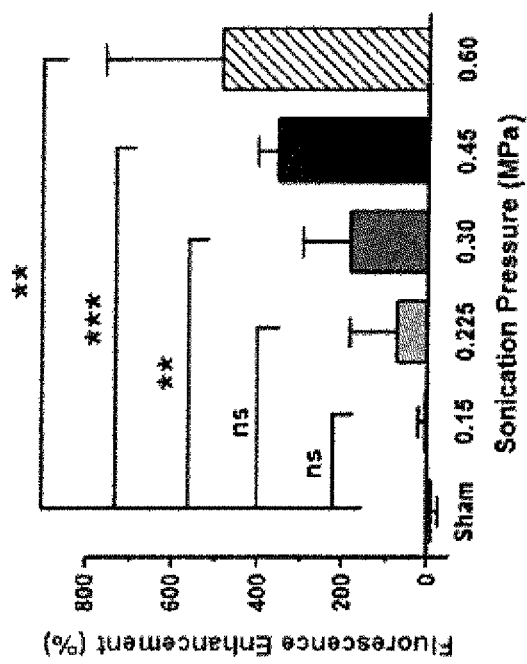

Following the systemic administration of microbubbles and subsequent BBB opening, a significant fluorescence enhancement was detected for all mice when sonicated at pressures including and above 0.30 MPa (P<0.0050). A similar inconsistency of dextran delivery across animals was seen at 0.225 MPa that only 3 out of 5 mice showed significant fluorescence enhancement in the targeted ROI. Thus, no sufficient statistical difference (P>0.16) could be obtained to unequivocally show BBB opening at pressures below 0.30 MPa (FIG. 7B). The detectable fluorescence signal was predominately contained within vessels at 0.30 MPa but more diffusely distributed throughout the targeted region at 0.45 MPa, indicating a more homogenous distribution of dextran molecules (FIGS. 8H and 8I). At 0.60 MPa, heterogeneous spots of particularly high levels of fluorescence in combination with diffusely distributed fluorescence was observed (FIG. 8J).

For each acoustic pressure, microbubbles produced greater fluorescence enhancement compared to nanodroplets. The normalized fluorescence enhancement with pressure amplitude followed a linear relationship with correlation coefficients at 0.76 and 0.94 for nanodroplets and microbubbles, respectively. The pressure threshold, at which significant fluorescence enhancement was detected in comparison to the sham animals, was higher for the nanodroplets (0.60 MPa) than that for the microbubbles (0.30 MPa), although the percent enhancement values at the threshold pressures were not statistically different (P=0.56).

For purpose of illustration and not limitation, as embodied herein, a contrast agent-dependent BBB opening threshold is provided. FIGS. 8A-J shows the quantitative acoustic emission results detected before and after the contrast agent administrations at various sonication pressures. For nanodroplets, the quantified SCD showed significant increase (P<0.0001) at 0.60 MPa (FIG. 9A), corresponding to the significant dextran delivery detected based on fluorescence microscopy. However, no statistical difference was determined at 0.45 MPa (P=0.21) despite a 90% mean signal increase after nanodroplet administration owing to the large variations among different mice. The SCD increase followed a linear relationship with the sonication pressure ($R^2=0.99$). The relative SCD percent increase before and after nanodroplet injection ranged between −46.4% and 395% for pressures 0.15-0.60 MPa. The quantified ICD, on the other hand, showed no detectable inertial cavitation dose across all pressures (FIG. 9B), implying that no significant vaporized nanodroplet fragmentation was detected during sonication.

Figure 9:
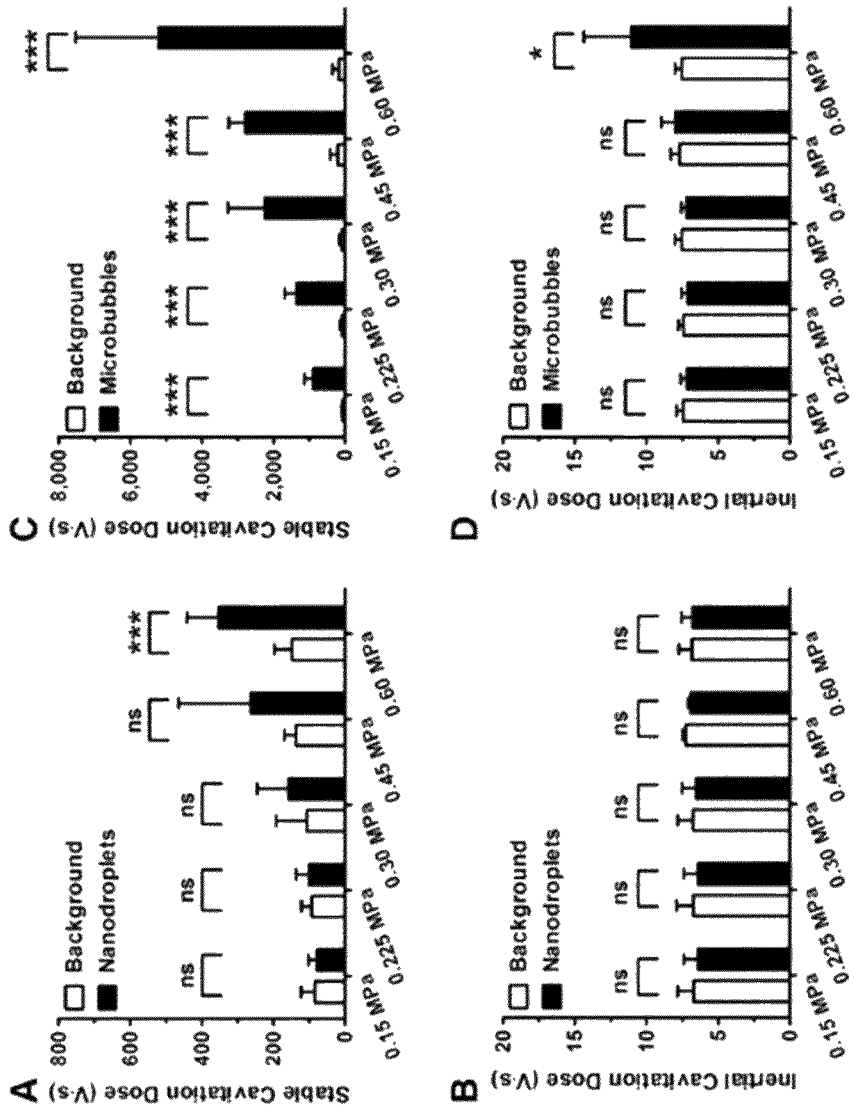
FIG. 9 illustrates quantified acoustic emission detected during BBB opening at various sonication pressures.

The acoustic emission results for the microbubble group are shown in FIGS. 9C and 9D. The SCD showed significant increase (P<0.0005) for all pressure levels after microbubble injections regardless the outcome of the BBB opening (FIG. 9C). Similar to the nanodroplet group, the SCD increase followed a linear correlation with the FUS pressure amplitude ($R^2=0.93$) with the relative percent increase ranging 532%-1117% for pressures 0.15-0.60 MPa, respectively. The ICD measurement showed significant signal increase after microbubble injection at 0.60 MPa (P=0.017) but not at other pressure levels, indicating microbubbles underwent inertial cavitation during sonication only at the highest acoustic energy exposure (FIG. 9D).

Figure 10:
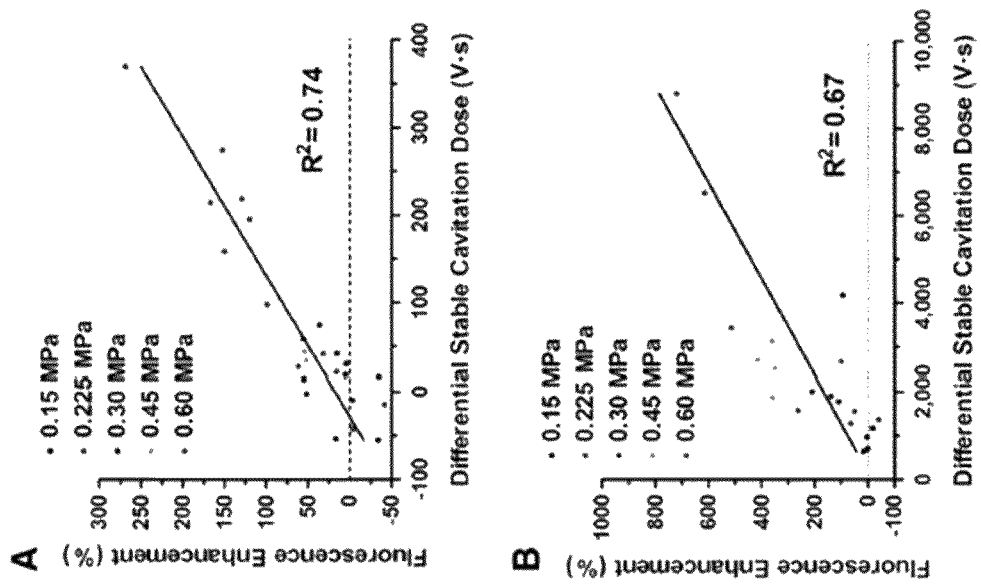
FIG. 10 illustrates the correlation between differential stable cavitation dose (SCD) and fluorescence enhancement.
Figure 11:
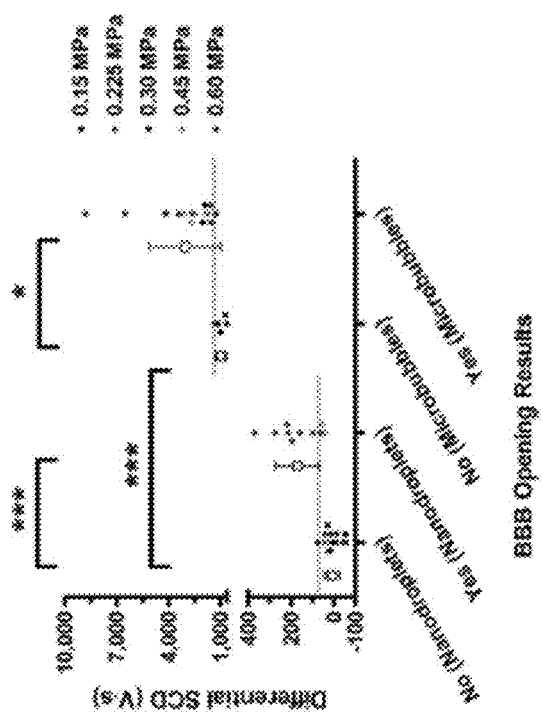
FIG. 11 illustrates the stable cavitation dose (SCD)-indicated BBB opening threshold.

In order to test whether acoustic emissions could be used to predict the magnitude of the BBB opening, the relative fluorescence enhancement was plotted against the SCD for all sonications using each contrast agent (FIGS. 10A-B). Both agents showed relatively good linear correlations between these two parameters ($R^2=0.74$ for nanodroplets and $R^2=0.67$ for microbubbles). A cavitation dose opening threshold can also be derived when SCD was grouped based on whether significant dextran delivery was detected based on fluorescence enhancement (FIG. 11). For the mice sonicated in the presence of nanodroplets, a statistically higher (P<0.0001) stable cavitation emission was detected for cases where significant fluorescence enhancement was measured. The highest SCD value, at which no evidence of dextran delivery was detected, was 74 V·$s^2$. Out of the 10 animals that showed significant fluorescence increase, 3 mice (30%)

had their SCD lower than 74 V·s², suggesting that this level could be used as the threshold for predicting successful FUS-induced BBB opening using nanodroplets as the contrast agents.

The acoustic threshold of BBB opening appeared to be contrast agent dependent. For the microbubble group, the highest SCD value, for which no detectable dextran delivery was observed, was 1.37 kV·s², significantly higher ($P<0.0001$) than the SCD threshold found for the nanodroplet group. A much more prominent threshold was held for group #2, for 1 out of 15 mice (6.7%) with significant fluorescence enhancement had a SCD lower than 1.37 kV·s². Despite the wider range of the calculated SCDs, in which successful BBB opening was detected, a statistical difference was obtained ($P=0.04$) between cases with or without significant dextran delivery. The threshold for predicting FUS-induced BBB opening in the presence of microbubbles was therefore concluded to be 1.37 k V·s² (FIG. 11).

Figure 12:
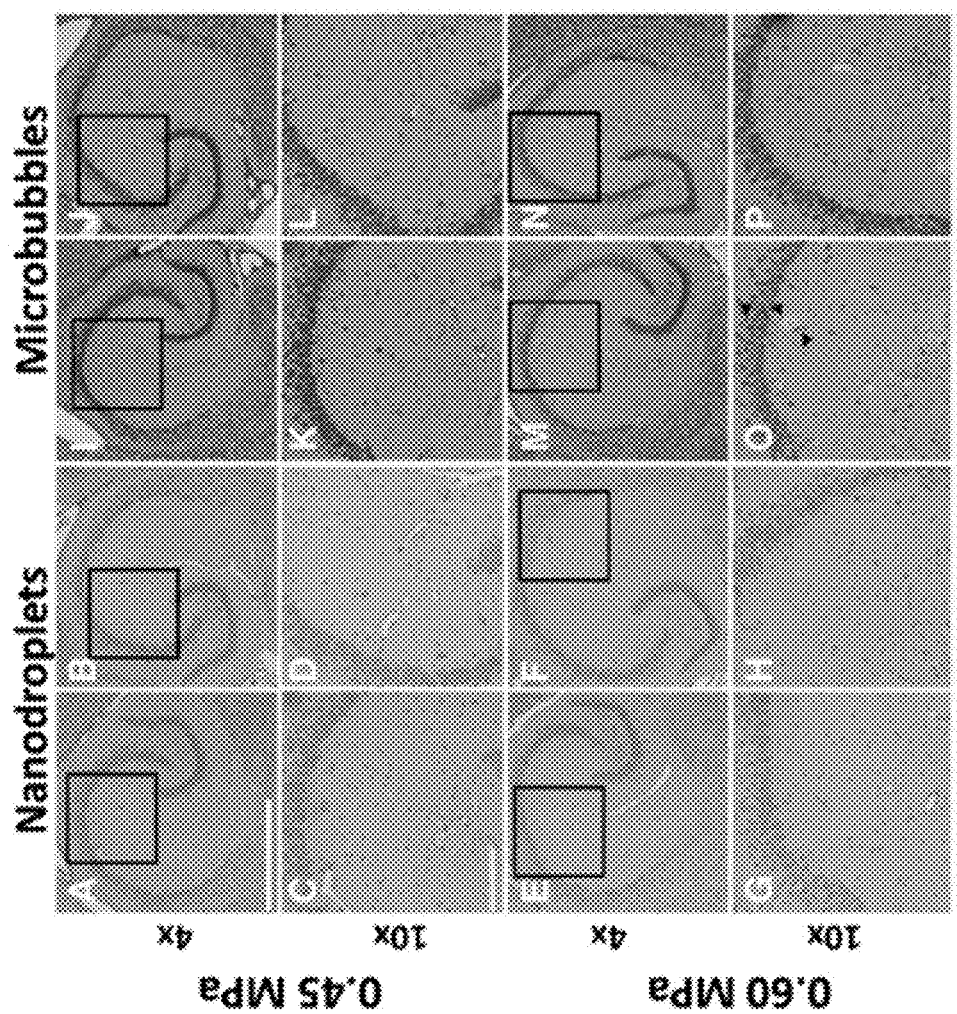
FIG. 12 shows representative histological images of the targeted and control hippocampi.

Histological evaluation was performed in order to assess for potential tissue damage caused by the procedure. FIGS. 12A-P shows the bright-field microscopic images taken of representative brain samples at 0.45 and 0.60 MPa. These two pressure amplitudes were chosen since relatively consistent BBB opening was detected only at these pressure levels for both nanodroplet and microbubble groups. Close examinations did not reveal any discrete damage sites, such as clusters of dark neurons, small erythrocyte extravasations, hemorrhage or microvacuolations at 0.45 MPa for either the nanodroplet or the microbubble group (FIGS. 12A-P, top). A few (<10) dark neurons were identified from 3 nonadjacent sections of the representative brain sample that was sonicated at 0.30 MPa using nanodroplets. No other tissue damage indicators were observed, indicating that this could be an artifact due to inadequate perfusion-fixation. However, small clusters of extravasated erythrocytes in addition to a few dark neurons were observed for a sample from the microbubble/0.60 MPa cohort (FIG. 12O). Less than 10 clusters were found throughout the sonicated region across all sections, indicating minor tissue damage. The larger portion of the targeted hippocampus appeared to be normal and the neurons appeared to be unaffected (FIG. 12M).

Figure 8:
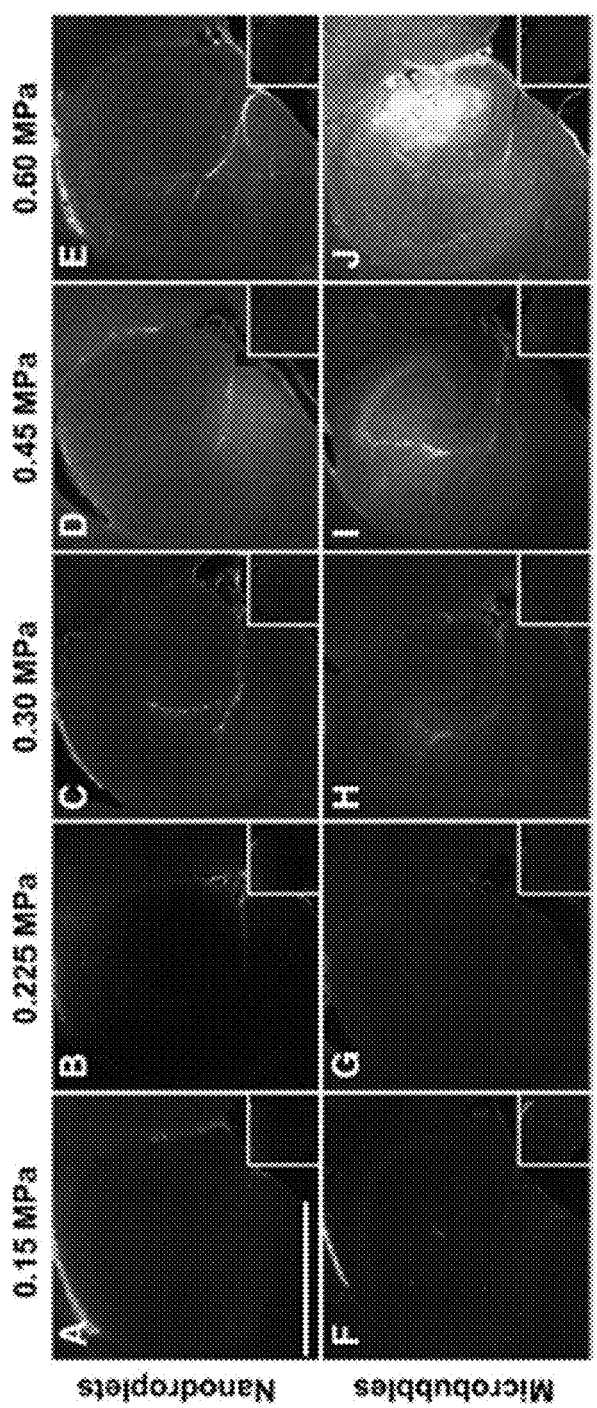
FIG. 8 includes representative fluorescence images comparing the targeted and the control (insets) hippocampi when nanodroplets (top) or microbubbles (bottom) were used to mediate BBB opening at various sonication pressures.

The current Example utilized acoustically-activated nanodroplets as a class of contrast agents to facilitate targeted drug delivery in the brain after FUS-induced BBB opening in mice. Using fluorescent dextran as a model drug, the extent of the BBB opening was quantified and compared between nanodroplets and the conventional contrast agent, i.e., microbubbles (FIGS. 7 and 8). The two agents were compositionally the same—having lipid-encapsulated perfluorobutane cores—but the nanodroplet approach afforded taking advantage of the benefits of both the liquid and gaseous state of the cores. The acoustic emission generated from the contrast agents during sonication was recorded and analyzed in order to gain insights to their cavitation characteristics (FIGS. 9A-D). A linear correlation between BBB permeabilization, as indicated by the relative fluorescence enhancement within the targeted hippocampus, and the acoustic emission, as characterized by the SCD, was found for both nanodroplets ($R^2=0.74$) and microbubbles ($R^2=0.67$) (FIGS. 10A-B). The acoustic threshold, at which significant dextran delivery was observed, appeared to be contrast agent dependent (FIG. 11).

The high-speed microscopy results confirmed that the nanodroplet samples were acoustically vaporizable at exposure conditions similar to that used during BBB opening in vivo (FIG. 6). The utilization of acoustically vaporized nanodroplets in this Example produced a similar homogenous dextran distribution throughout the targeted volume and was more prominent when compared to microbubbles under the same acoustic exposure settings (FIGS. 8D-8J).

Initial histological examinations confirmed the safety for the nanodroplet-mediated FUS-induced BBB opening technology. In comparison to nanodroplets, microbubble-mediated BBB opening resulted minor tissue damage at the targeted region for both brain samples evaluated from the 0.60 MPa cohort (FIG. 12O). Based on the H&E staining results, it is reasonable to conclude that the significantly increased dextran delivery at 0.60 MPa was to be caused by the increased magnitude of disruption at the focal region.

Passively detected acoustic emissions originated from the oscillating contrast agents could be used to characterize the type of cavitation events occurred during sonication, providing insights to the mechanism of the FUS-induced BBB opening. Only an increase in the harmonics and ultraharmonics signals detected after nanodroplet administration at all pressures, suggesting that the vaporized nanodroplet underwent mainly nonlinear stable cavitation during sonication. The quantified SCD showed significant increase at the highest pressure amplitude (0.60 MPa), indicating that a minimum SCD threshold was needed to induce BBB opening. When microbubbles were used as the contrast agent, significant SCD increase was seen across all sonication pressures regardless of the outcome of BBB opening. The SCD value for the microbubble group at the lowest pressure (902 V·s² at 0.15 MPa) was much higher than that for the nanodroplet group even at the highest pressure (353 V·s² at 0.60 MPa), suggesting that the SCD threshold was contrast agent-dependent. This result was further demonstrated in FIG. 11, in which significant difference was calculated between threshold baselines (i.e., negative cases for which no dextran delivery was observed).

Example 2

For purpose of illustration and not limitation, delivery of drugs through FUS in combination with microbubbles and intranasal (IN) delivery were combined for enhancing the delivery efficiency of IN administered drugs at a targeted location (FUS+IN). After IN administration of 40 kDa fluorescently-labeled dextran as the model drug, FUS targeted at one region within the caudate putamen of mouse brains was applied in the presence of systemically-administered microbubbles. To compare the FUS-alone technique, in which intravenous (IV) drug injection was employed (FUS+IV), FUS was also applied after IV injection of the same amount of dextran in another group of mice. Dextran delivery outcomes were evaluated using fluorescence imaging of brain slices. The results showed that FUS+IN enhanced drug delivery within the targeted region compared with that achieved by IN only. The delivery efficiency by FUS+IN was not significantly different from FUS+IV. Accordingly, FUS+IN can be an alternative strategy for targeted brain drug delivery. FUS+IN can therefore be used for treating a variety of CNS diseases.

For purpose of illustration and not limitation, as embodied herein, IV injection of the therapeutic agents with microbubbles was performed, and then FUS was utilized to induce BBB opening for drug delivery. The FUS focuses externally generated ultrasound pulses through the skull onto a small focal region (on the order of millimeters) deep into the subcortical structures, which allows highly precise and noninvasive targeting of brain regions where treatment is desired. Microbubbles are micron-scale gas bubbles stabilized by a lipid, protein, albumin or polymer shell.

A total of 26 male C57BL/6 mice (Harlan Laboratories; Indianapolis, Ind.) weighing 20-25 g were used. Among these 26 mice, 20 were divided into the following four experimental groups with n=5 for each group. (1) Control group: no dextran delivery and no FUS applied. (2) IN sham group: IN administration of the dextran without FUS. (3) IN treatment group: IN administration of the dextran with FUS applied on the left side of the caudate putamen while the contralateral right side was not sonicated. (4) IV treatment group: IV administration of the dextran with FUS applied on the left side of the caudate putamen while the contralateral right side was not sonicated. To assess the safety of FUS treatment, 6 more mice were treated following the same protocol as group #3 or #4 with n=3 for each group. All procedures were approved by the Columbia University Institutional Animal Care and Use Committee.

Microbubbles comprised of a 90 mol % 1,2-distearoyl-sn-glycero-3-phosphocholine (OS PC) and 10 mol % 1,2-distearoyl-sn-glycero-3-phosphoethanolamine-N-[methoxy (polyethylene glycol)2000] (DSPE-PEG2000) (Avanti Polar Lipids, Alabaster, Ala., USA) lipid-shell and a perfluorobutane (FluoroMed, Round Rock, Tex., USA) gas-core were manufactured. Size-selected microbubbles with a median diameter of 4-5 µm were isolated from a poly-dispersed microbubble distribution using a differential centrifugation method. Their size distribution and concentrations were determined by a particle counter (Multisizer III, Beckman Coulter Inc.; Opa Locka, Fla., USA). Before each injection into the mouse, their concentrations were diluted using sterile saline to a final concentration of approximately $8 \times 10^8$ number of microbubbles per mL.

For the control group (group #1), no dextran was administered.

For IN sham group (group #2) and IN treatment group (group #3), ~2 mg of 40 kDa Texas Red-labeled dextran (Life Technologies Inc., Grand Island, N.Y., USA) was administered intranasally. The dextran was dissolved in saline at a concentration of 40 mg/mL. The anaesthetized mice were placed supine with the head position stabilized horizontally. A micropipette was used to intranasally administer 3 µL drops of the dextran solution to alternating nostril every 2 minutes. Drops were placed at the opening of the nostril, allowing the animal to snort each drop into the nasal cavity. A total of 51 µL of dextran solution (~2 mg dextran) was delivered over the course of 34 minutes.

For the IV treatment group (group #4), the same amount of dextran (51 µL in volume, 40 mg/mL in concentration, and ~2 mg in dose) was injected through the tail vein.

Figure 13:
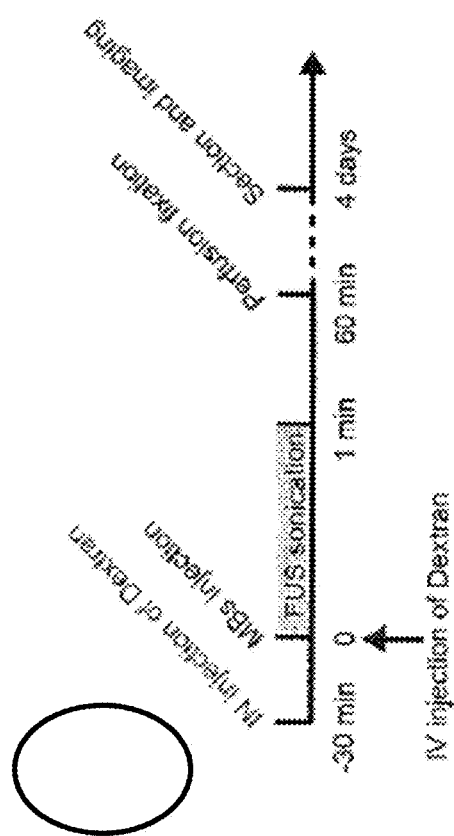
FIG. 13 illustrates an experimental timeline.

For the IN treatment group (group #3) and IV treatment group (group #4), the mice were sonicated at a targeted brain location using an experimental setup illustrated in FIG. 4 and following an experimental timeline shown in FIG. 13.

A single-element FUS transducer (center frequency: 1.5 MHz, focal depth: 60 mm; diameter: 60 mm; !masonic, Besancon, France) was driven by a function generator (33220A; Agilent, Palo Alto, Calif., USA) through a nominal 50 dB gain power amplifier (325LA; E&l, Rochester, N.Y., USA). The lateral and axial dimensions of the FUS focal region measured in water were 1.2 mm and 13.0 mm. A custom-built truncated cone was attached to the transducer and filled with degassed water to provide acoustic coupling. The cone was immersed in a degassed-water container. The bottom of the water container had a window sealed with an almost acoustically and optically transparent membrane. The container was placed on the mouse head and coupled with degassed ultrasound gel. Acoustic emissions arising from microbubble cavitation were acquired by a pulse-echo transducer (center frequency 10 MHz; focal length 60 mm; Olympus NDT, Waltham, Mass., USA), which was positioned through a central hole of the FUS transducer and confocally aligned with the FUS transducer. The signals received by the pulse-echo transducer were amplified by 20 dB (Model 5800; Panametrics-NDT, Waltham, Mass., USA) and then digitized (Razor Express CompuScope 1422; Gage Applied Technologies, Inc., Lachine, QC, Canada) at a sampling frequency of 50 MHz.

Before FUS sonication, each mouse was positioned prone with its head immobilized by a stereotaxic frame (David Kopf Instruments, Tujunga, Calif., USA). Hairs on the mouse head were removed with an electric clipper and a depilatory cream. A modified 27Gx½ butterfly catheter (Terumo Medical; Somerset, N.J., USA) was inserted into the tail vein for IV injection. The FUS transducer was moved 2 mm lateral of the sagittal suture and 6 mm anterior of the lambdoid suture using a grid positioning method. Freshly diluted microbubble suspension (30 µL) was bolus injected via the tail vein prior to each sonication. For the IV treatment group (group #4), the microbubbles were co-injected with the dextran (FIG. 13). Immediately after the injection (~5 s), pulsed FUS (center frequency: 1.5 MHz; peak-negative pressure: 0.45 MPa; pulse length: 6.7 ms; pulse repetition frequency: 5 Hz; duration: 1 min) was applied transcranially to the left caudate putamen. The non-sonicated right caudate putamen served as control for IN administration only (group #3) or IV injection only (group #4). Prior to microbubble injection, a 30-s sonication using the same acoustic parameters was applied in order to measure the baseline background cavitation signals, needed in the acoustic emission analysis described herein.

For all the mice used in the current Example, a 1-h period was allowed after the end of IN and IV dextran administration to enable the dextran to circulate throughout the vasculature and to diffuse into the brain parenchyma (FIG. 13). At the end of the allotted time, the animal was sacrificed by transcardial perfusion. The mouse brains were processed and prepared for either frozen (60 µm thick) or paraffin (6 µm thick) sections. The frozen sections were imaged by a fluorescence microscope (BX61; Olympus, Melville, N.Y., USA) and used later for quantifying dextran delivery outcomes. The paraffin sections were used for whole brain histological examinations by hematoxylin and eosin (H&E) staining.

To quantify the stable and inertial cavitation behaviors of the microbubbles within the FUS targeted region, stable cavitation dose and inertial cavitation dose were calculated, respectively. The stable cavitation dose was quantified based on the peak amplitude of the frequency spectrum around each harmonic frequency of each pulse in the range between 3 and 9 MHz. The inertial cavitation does was quantified based on the broadband emission. The net emissions from the microbubbles were then determined by subtracting the corresponding doses calculated based on background signals acquired prior to microbubble injection.

The dextran delivery outcomes were determined by quantifying the fluorescence intensities within the targeted caudate putamen. Nine horizontal sections with four dorsal sections, four ventral sections, and a reference midline section were selected from each brain for analysis. All the fluorescence images were first normalized by their corresponding exposure time. Then, a circular region-of-interest (ROI, diameter=1.2 mm) was manually aligned with the sonicated and control caudate putamen on each section, and the spatial average fluorescence intensity within the ROI was calculated using ImageJ (National Institutes of Health;

Bethesda, Md.). The diameter of the ROI was selected to be the same as the FUS transducer lateral focal region dimension. The reported fluorescence enhancement was the sum of the calculated fluorescence intensities within the ROI of all nine sections.

An unpaired two-tailed Student's t-test using GraphPad Prism (Version 5.0°, La Jolla, Calif., USA) was used to compare between groups. A P value of 0.05 was considered to represent a significant difference in all the analyses. All data were expressed as mean±standard deviation.

Figure 14:
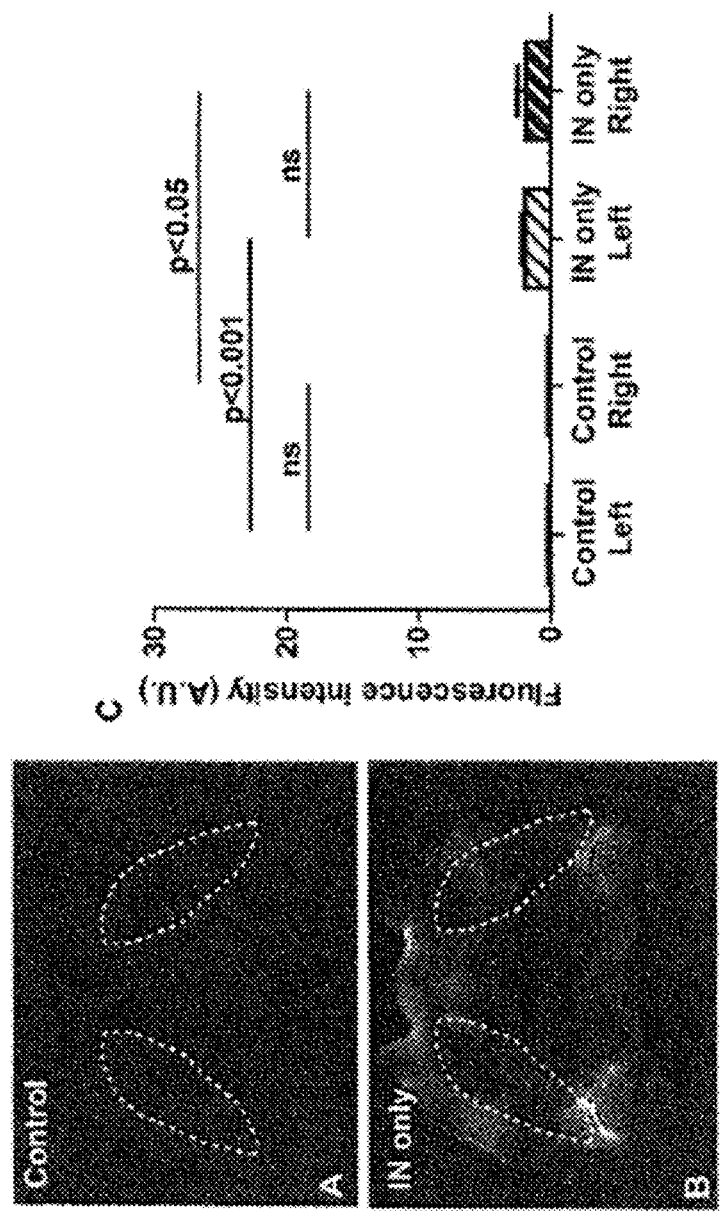
FIGS. 14A and 14B include representative fluorescence images of the whole brain horizontal section from the control treatment group (no FUS and no dextran administration) and the IN sham group (IN administration without FUS), respectively.
FIG. 14C depicts quantitative analysis of the fluorescence intensities.

FIGS. 14A and 14B present representative fluorescence images of horizontal sections of the whole brain from the control group (group #1) and IN sham group (group #2). As shown in FIG. 14B, IN administration of the dextran without FUS resulted in an elevation of dextran concentration in the whole brain. Statistically significant increase in the fluorescence intensity was found between these two groups (FIG. 14C), suggesting that IN administration alone could allow dextran to gain direct access to the brain. Within each group, no difference was found between left and right caudate putamen regions. However, the delivered dextran did not accumulate in any particular brain region and concentration achievable in different regions of the brain varied, confirming that IN administration is non-targeted.

Figure 15A:
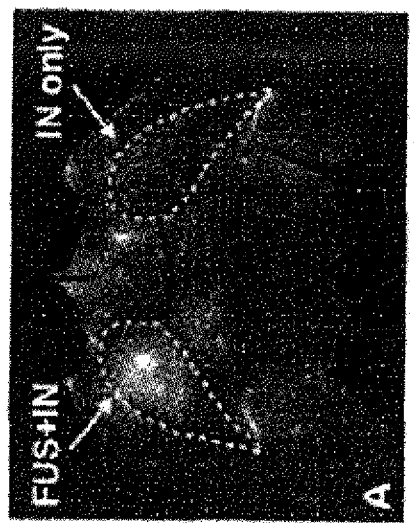
FIGS. 15A and 15B include representative fluorescence images of the whole brain horizontal section from the FUS+IN treatment group and the FUS+IV treatment group, respectively.

FIG. 15A shows that FUS exposure in the presence of microbubbles enhanced IN delivery at the targeted left caudate putamen when compared with the contralateral right side with IN administration only. Quantification of the fluorescence intensities found an increase of 8-folds in the fluorescence intensity compared with the contralateral control side (FIG. 15C).

Figure 15B:
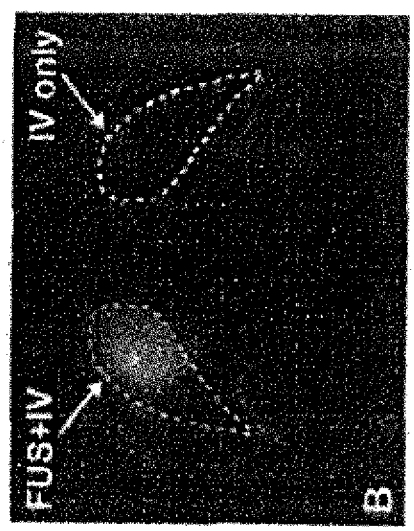
Figure 15C:
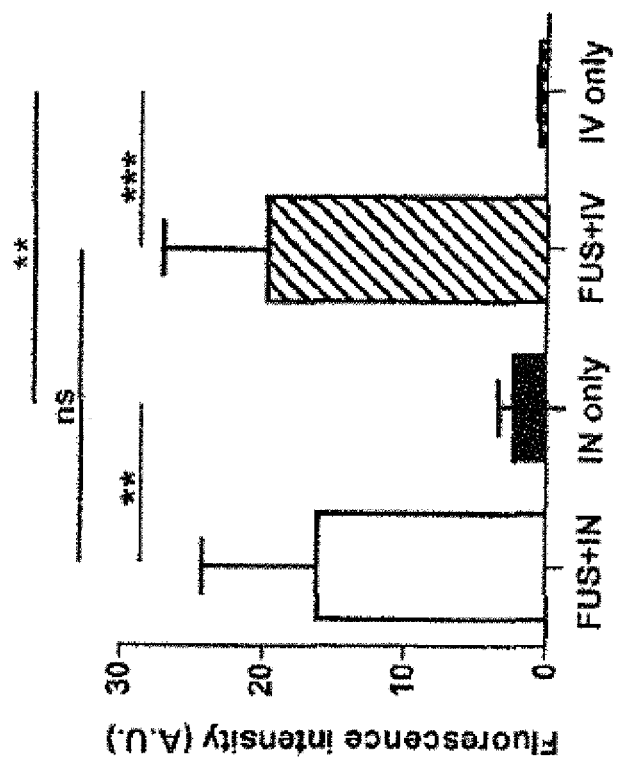
FIG. 15C depicts quantitative analysis of the fluorescence intensities.

When IV injection was used for the delivery of dextran instead of IN, similar localized dextran accumulation was observed at the targeted caudate putamen (FIG. 15B). In FIGS. 15A and 15B, the quantified fluorescence intensities of the FUS sonicated sides were 27.2 and 12.9 respectively. Thus, higher drug delivery efficiency at the targeted region was achieved in the FUS+IN case shown in FIG. 15A than the FUS+IV case shown in FIG. 15B. However, when comparing across the whole group, the administration route did not appear to affect the delivery efficiency in the targeted caudate putamen as no significant dextran accumulation was detected between FUS+IN and FUS+IV groups (P=0.048; FIG. 15C).

Although IN administrated drugs distribute to the whole brain, by adjusting the IN administration dose FUS+IN can achieve therapeutic drug level only within the targeted site while keeping non-targeted sites at sub-therapeutic level. Therefore, FUS can (1) break the restriction that IN route can only be used for particularly potent substances and (2) achieve targeted brain drug delivery.

Example 3

For purpose of illustration and not limitation, as embodied herein, nanodroplets were delivered intranasally and combined with focused ultrasound to enhance the delivery efficiency of IN-administrated drugs. By replacing IV injection of the microbubbles with IN administration of nanodroplets, the technique is completely noninvasive (needle-free and surgery-free). In contrast, microbubbles are constrained within the vasculature, and IV injection can be utilized for microbubble administration due to the relatively large size of the microbubbles.

The nanodroplets can be made as described herein, and as embodied herein, were made with similar shell and gas cone components as microbubbles. After IN administration, the nanodroplets can directly enter the brain through the nose-brain pathway without going through the blood circulation. The nanodroplets can be activated by FUS to form microbubbles at a targeted location, thereby enhancing IN drug delivery efficiency at the targeted location. Drugs can be administered separated after FUS sonication or administered with the nanodroplets before FUS sonication.

Figure 16:
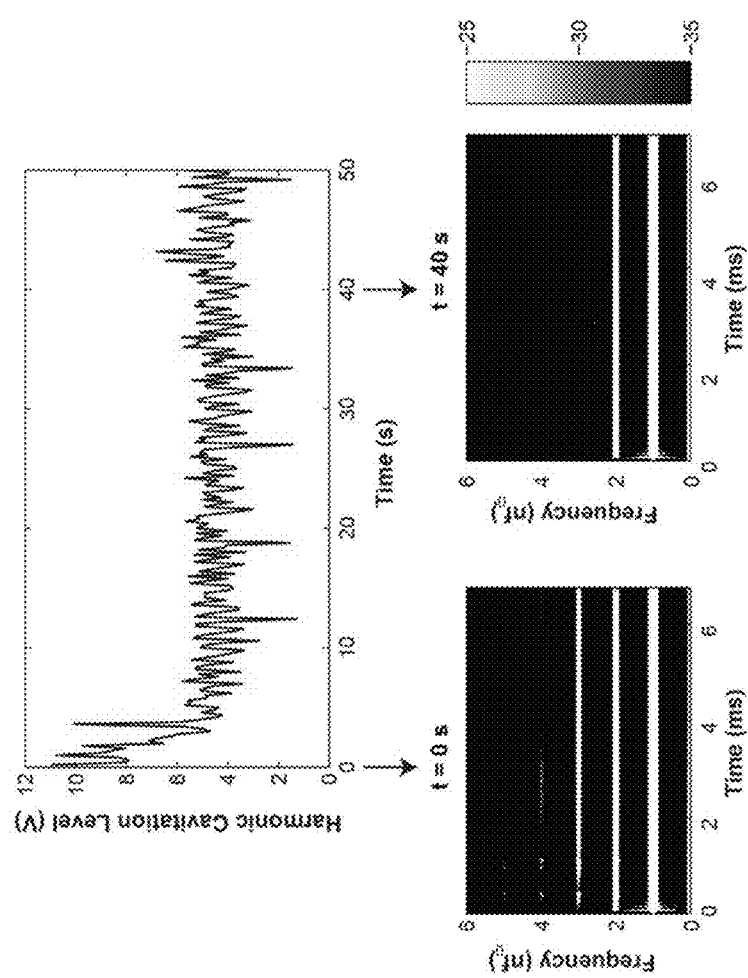
FIG. 16 depicts the harmonic cavitation level and spectrograms at time t=0 s and t=40 s.

Nanodroplets can be successfully delivered to the brain through the nose route, and the delivered nanodroplets can be activated by FUS. FIG. 16 shows stable cavitation, quantified by the harmonic cavitation level and indicated by the higher harmonics (above $2^{nd}$ harmonics) in the spectrogram, was detected at the beginning of FUS sonication after IN administration of nanodroplets.

Example 4

Figure 17:
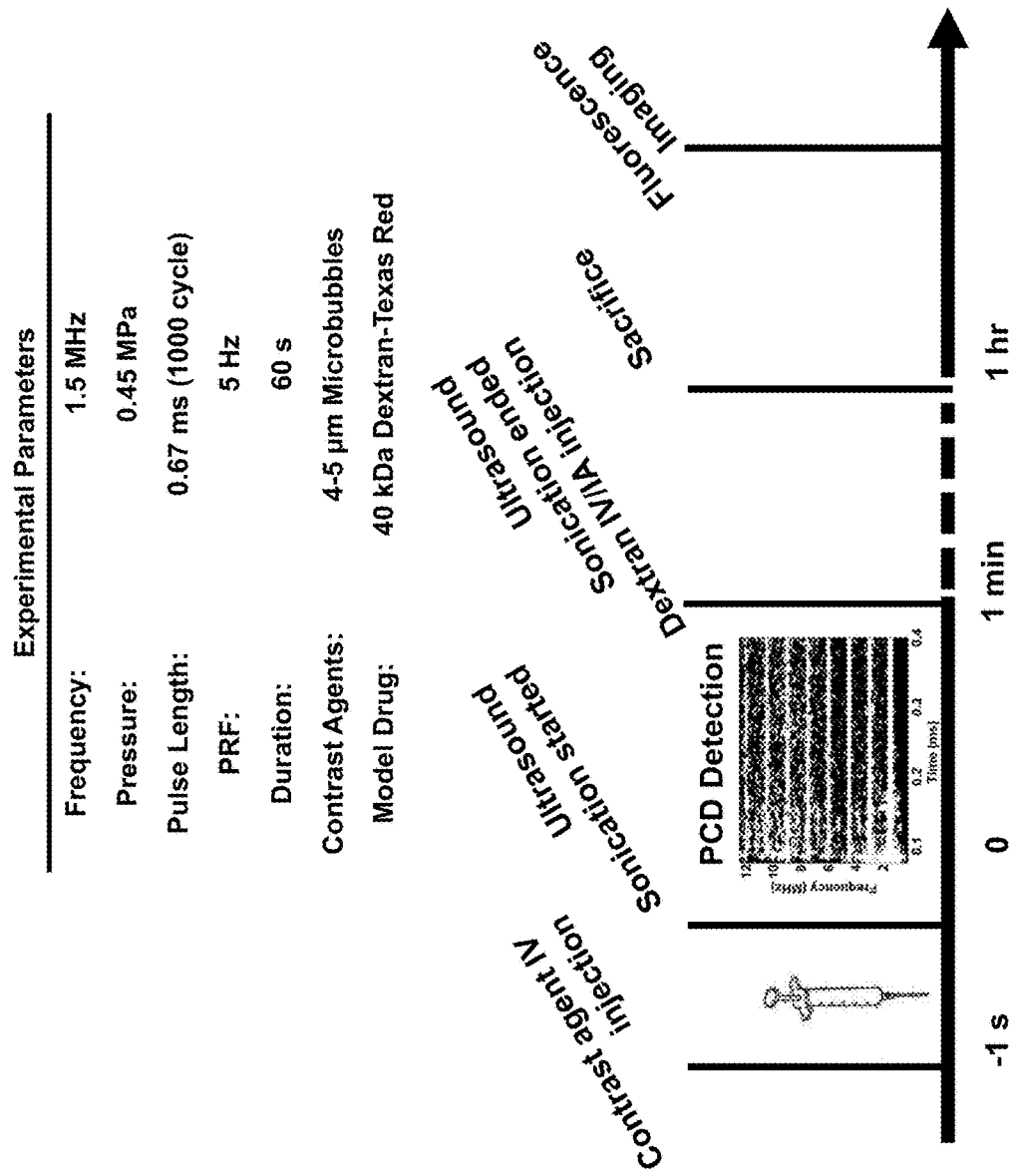
FIG. 17 illustrates experimental parameters and an experimental timeline
Figure 18:
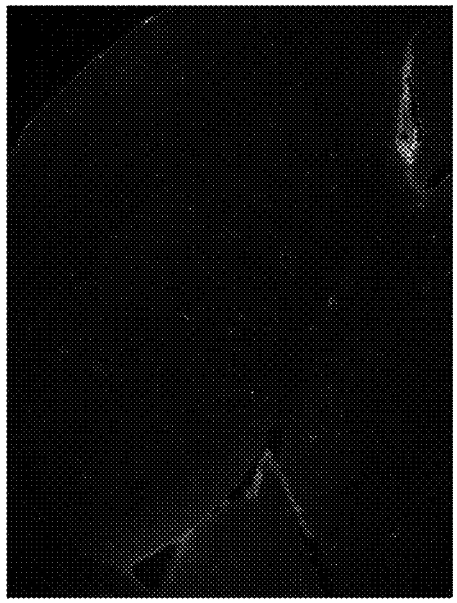
FIG. 18 includes representative fluorescence images of the whole brain horizontal section from the intravascular group and the intra-arterial group.
Figure 18:
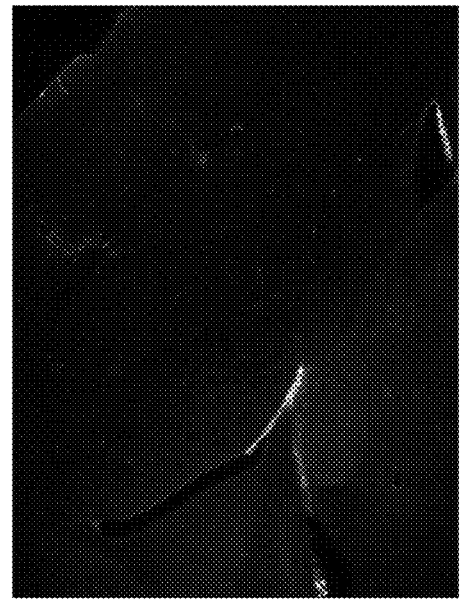
Figure 18:
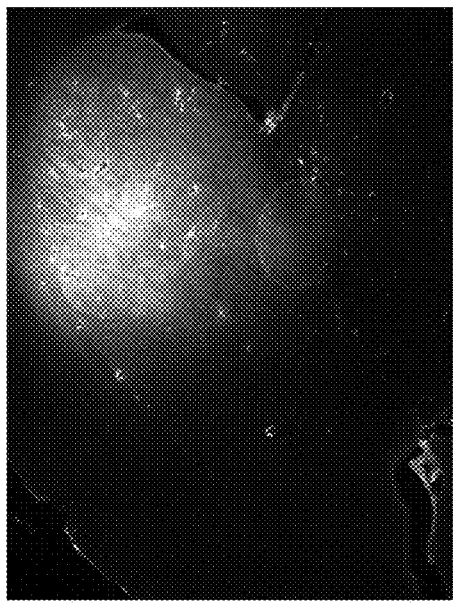
Figure 18:
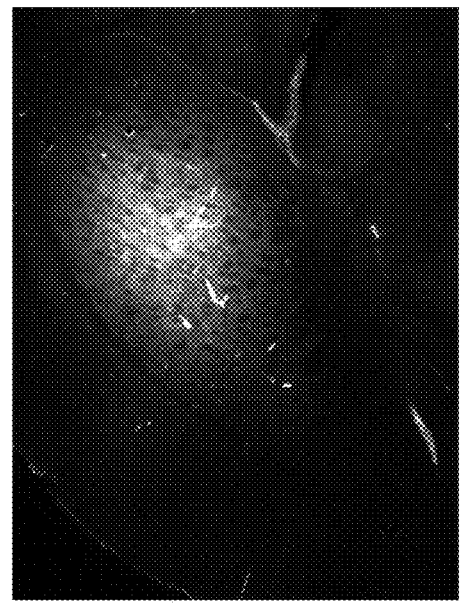
Figure 19:
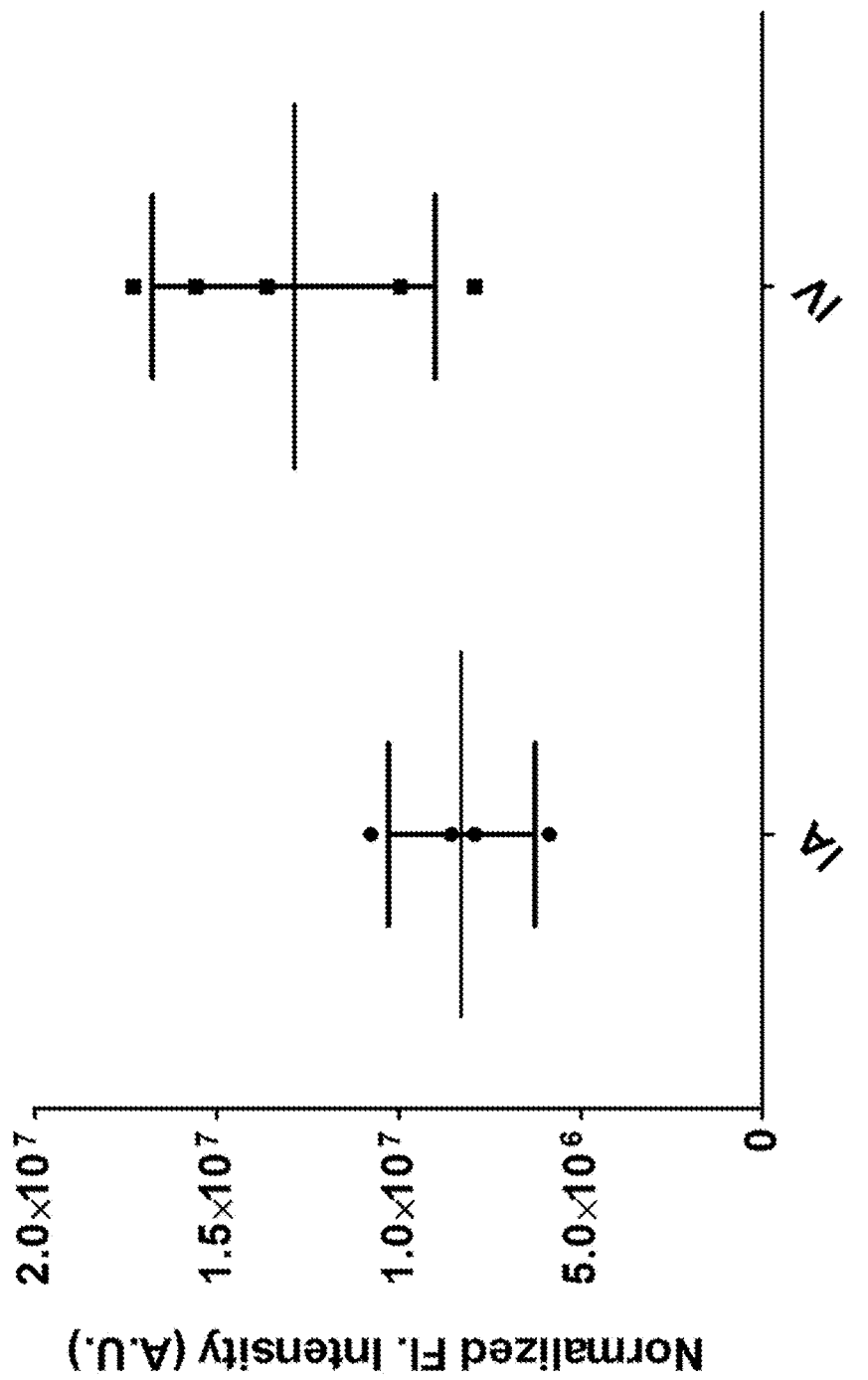
FIG. 19 depicts quantitative analysis of the fluorescence images of the whole brain.
Figure 20:
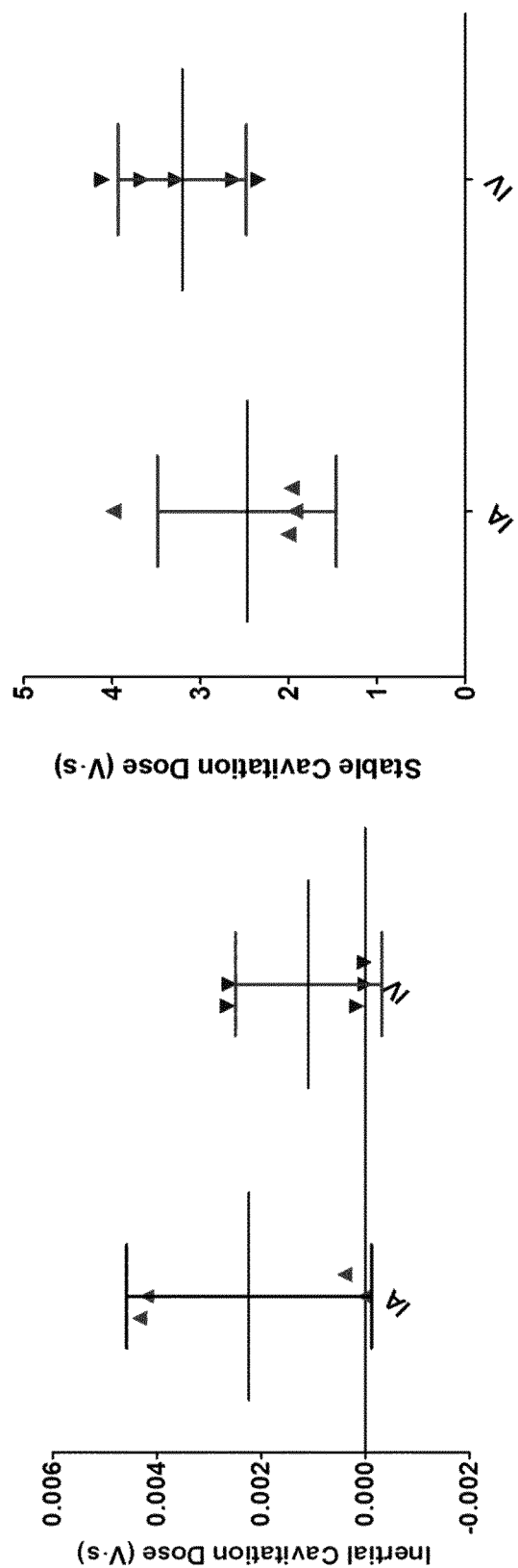
FIG. 20 illustrates initial cavitation dose and stable cavitation dose for the intravascular group and the intra-arterial group.

For purpose of illustration and not limitation, as embodied herein, intra-arterial delivery of the pharmaceutical compound was shown to results in similar drug delivery as intravascular drug delivery. Mice where given an intravenous or an intraarterial delivery of a pharmaceutical compound, in combination with FUS. FIG. 17 shows the experimental parameters and experimental timeline. FIG. 18 shows representative fluorescence images of horizontal sections of the whole brain for the intravenous group and the intraarterial group. FIG. 19 illustrates that the normalized fluorescence intensity was similar for both groups. FIG. 20 illustrates that the inertial cavitation dose and the stable cavitation dose were also similar for both groups.

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter can be discussed herein, or shown in the drawing of one of the embodiments and not in another embodiment, it should be apparent that individual features of one embodiment can be combined with one or more features of another embodiment or features from a plurality of embodiments. Thus, the foregoing description of specific embodiments of the disclosed subject matter has been presented for purposes of illustration and description. It is not intended to be exhaustive or to limit the disclosed subject matter to those embodiments disclosed.

The invention claimed is:

1. A method of delivering a therapeutic agent through a blood vessel having a blood brain barrier to a target location in a brain, comprising:
    targeting a region of the blood vessel proximate the target location in the brain;
    selecting a plurality of nanodroplets configured to vaporize at an acoustic pressure suitable to open the blood brain barrier with microbubbles, wherein the nanodroplets are separate from the therapeutic agent;
    delivering the plurality of nanodroplets to the region;
    delivering the therapeutic agent to the region;
    applying an ultrasound beam at the region at the acoustic pressure such that the nanodroplets vaporize, or cavitate, or convert to microbubbles that cavitate, thereby causing the blood brain barrier to open and allowing the therapeutic agent to diffuse out of the blood vessel through the open blood brain barrier and to the target location in the brain.

2. The method of claim 1, wherein the therapeutic agent is selected from the group consisting of antibodies, neural stem cells, siRNA, chemotherapeutic molecules, adenoviral vectors and neurotrophic factors.

3. The method of claim 1, wherein the nanodroplets each have a diameter between 100 nm and 300 nm.

4. The method of claim 1, wherein the nanodroplets each have a diameter between 150 nm and 250 nm.

5. The method of claim 1, wherein the ultrasound beam has a sonication pressure greater than 0.45 MPa.

6. The method of claim 1, wherein the ultrasound beam has a sonication pressure greater than 0.6 MPa.

7. The method of claim 1, wherein delivering the nanodroplets comprises at least one injection of the nanodroplets.

8. The method of claim 7, wherein the injection is an intravenous injection.

9. The method of claim 7, wherein the injection is an intraarterial injection.

10. The method of claim 1, wherein delivering the nanodroplets comprises delivering the nanodroplets intranasally.

11. The method of claim 1, wherein delivering the therapeutic agent comprises at least one injection of the therapeutic agent.

12. The method of claim 11, wherein the injection is an intravenous injection.

13. The method of claim 11, wherein the injection is an intraarterial injection.

14. The method of claim 1, wherein delivering the therapeutic agent comprises delivering the therapeutic agent intranasally.

15. The method of claim 1, wherein delivering the nanodroplets and applying the ultrasound beam are performed simultaneously.

16. The method of claim 1, wherein the nanodroplets are a microbubble condensation process.

17. A method of delivering a therapeutic agent through a blood vessel having a blood brain barrier to a target location in a brain of a patient, comprising
delivering the therapeutic agent intranasally;
selecting a plurality of nanodroplets configured to vaporize at an acoustic pressure suitable to open the blood brain barrier with microbubbles, wherein the nanodroplets are separate from the therapeutic agent;
targeting a region of a blood vessel proximate the target location in the brain;
delivering the plurality of nanodroplets into the patient such that the nanodroplets travel to the region of the blood vessel;
applying an ultrasound beam at the region such that the nanodroplets vaporize, or cavitate, or convert to microbubbles that cavitate, thereby generating mechanical effects on the blood vessel and enhancing delivery of the therapeutic agent.

18. The method of claim 17, wherein the mechanical effects include at least one of high shear stress, microstreaming, and microjeting the blood vessel, thereby allowing transvascular delivery of the therapeutic agent.

19. The method of claim 17, wherein the mechanical effects include pushing and pulling surrounding tissue, thereby causing bulk fluid flow in perivascular spaces.

20. The method of claim 17, wherein the ultrasound beam comprises a center frequency of about 1.5 MHz, a peak-negative pressure of about 0.45 MPa, a pulse length of about 6.7 ms, a pulse repetition frequency of about 5 Hz, and a duration of about 1 minute.

21. The method of claim 17, wherein the therapeutic agent is disposed at the target location in the brain at a supra-therapeutic level and the therapeutic agent is disposed elsewhere in the brain at a sub-therapeutic level.

22. The method of claim 17, wherein delivering the nanodroplets and applying the ultrasound beam are performed simultaneously.

23. The method of claim 17, wherein delivering the therapeutic agent and applying the ultrasound beam are performed simultaneously.

24. The method of claim 17, wherein applying the ultrasound beam is performed prior to delivering the therapeutic agent.

25. The method of claim 17, wherein the nanodroplets are delivered intranasally.

26. The method of claim 17, wherein the nanodroplets are generated by a microbubble condensation process.

* * * * *

UNITED STATES PATENT AND TRADEMARK OFFICE
CERTIFICATE OF CORRECTION

PATENT NO. : 10,322,178 B2
APPLICATION NO. : 14/457023
DATED : June 18, 2019
INVENTOR(S) : Chen Chen, Elisa E. Konofagou and Paul Dayton It is certified that error appears in the above-identified patent and that said Letters Patent is hereby corrected as shown below:

In the Specification

In Column 1, Lines 15-22, under the heading, GRANT INFORMATION please correct:
"This invention was made with government support under Grant Nos. R01 EB009041, R01 AG038961, R21 EB011704, and S10 RR025594, awarded by the National Institutes of Health, Grant No. DMR 1122483 awarded by the National Science Foundation, a NSF Graduate Research fellowship and a grant by the Kinetics Foundation. The U.S. government has certain rights in this invention."

GRANT INFORMATION should read:
-- This invention was made with government support under grants AG038961 and EB009041 awarded by the National Institutes of Health. The Government has certain rights in this invention. --

Signed and Sealed this
Fifth Day of September, 2023

Katherine Kelly Vidal
*Director of the United States Patent and Trademark Office*